US008362043B2

(12) United States Patent
Charrier et al.

(10) Patent No.: US 8,362,043 B2
(45) Date of Patent: Jan. 29, 2013

(54) CASPASE INHIBITORS AND USES THEREOF

(75) Inventors: Jean-Damien Charrier, Wantage (GB);
Ronald Knegtel, Abindgon (GB);
Michael Mortimore, Burford (GB);
John R. Studley, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1236 days.

(21) Appl. No.: 11/284,366

(22) Filed: Nov. 21, 2005

(65) Prior Publication Data

US 2006/0160862 A1 Jul. 20, 2006

Related U.S. Application Data

(60) Provisional application No. 60/630,926, filed on Nov. 24, 2004.

(51) Int. Cl.
*A61K 31/4425* (2006.01)
*C07D 213/75* (2006.01)
(52) U.S. Cl. .................. 514/349; 546/297
(58) Field of Classification Search ............. 546/297; 514/349
See application file for complete search history.

(56) References Cited

U.S. PATENT DOCUMENTS

| 5,756,466 | A | 5/1998 | Bemis et al. |
|---|---|---|---|
| 5,847,135 | A | 12/1998 | Bemis et al. |
| 6,184,244 | B1 | 2/2001 | Karanewsky et al. |
| 6,197,750 | B1 | 3/2001 | Karanewsky et al. |
| 6,242,422 | B1 | 6/2001 | Karanewsky et al. |
| 2003/0232846 | A1 | 12/2003 | Golec et al. |
| 2004/0048797 | A1 | 3/2004 | Miller et al. |
| 2004/0072850 | A1 | 4/2004 | Knegtel et al. |
| 2004/0192612 | A1 | 9/2004 | Charrier et al. |
| 2004/0242494 | A1 | 12/2004 | Brenchley et al. |
| 2007/0155718 | A1 | 7/2007 | Durrant et al. |

FOREIGN PATENT DOCUMENTS

| EP | 0509769 B1 | 9/1996 |
|---|---|---|
| EP | 0826671 B1 | 12/2004 |
| WO | WO 95/26958 A1 | 10/1995 |
| WO | WO 95/35308 A1 | 12/1995 |
| WO | 98/16502 A1 | 4/1998 |
| WO | 00/61542 A1 | 10/2000 |
| WO | WO 01/42216 A2 | 6/2001 |
| WO | WO 2004/106304 A2 | 12/2004 |

OTHER PUBLICATIONS

Patani et al., "Bioisosterism: A rational, etc.," Chem. Rev., 1996, 96, 3147-3176.*
Semple, Graeme et al., "Pyridone-Based Peptidomimetic Inhibitors of Interleukin-Iβ-Converting Enzyme (ICE)," Bioorganic & Medical Chemistry Letters, Oxford, Great Britain, vol. 7, No. 10, May 20, 1997, pp. 1337-1342, XP004136329, ISSN: 0960-894X.
Dragovich Peter S., et al., "Structure-Based Design, Synthesis, and Biological Evaluation of Irreversible Human Rhinovirus 3C Protease Inhibitors. 6. Structure—Activity Studies of Orally Bioavailable, 2-Pyridone-Containinig Peptidomimetics," Journal of Medicinal Chemistry, American Chemical Society, Washington US, vol. 45, No. 8, 2002, pp. 1607-1623, XP002344347, ISSN: 0022-2623.
Office Action Dated Dec. 17, 2007 from U.S. Appl. No. 10/855,699.
Warner, et al., "Non-peptide Inhibitors of Human Leukocyte Elastase. 1. The Design and Synthesis of Pyridone-Containing Inhibitors," J. Med. Chem. 37:3090-3099 (1994).
Ellis et al., "Mechanisms and functions of cell death", Annual review cell biology, 7, 663, (1991).
Hiroyuki Yaoita et al., "Attenuation of ischemia/reperfusion injury in rats by a caspase inhibitor", Circulation, 97, 276-281 (1998).
Yu Cheng et al., "Caspase inhibitor affords neuroprotection with delayed administration in a rat model of neonatal hypoxic-ischemic brain injury", Journal of Clinical Investigation, 101, 1992-1999 (1998).
Alexander G. Yakovlev et al., "Activation of CPP32-like caspases contributes to neuronal apoptosis and neurological dysfunction after traumatic brain injury", The Journal of Neuroscience, 17, 7415-7424, (1997).
Ivan Rodriguez et al., "Systemic injection of a tripeptide inhibits the intracellular activation of CPP32-like proteases in vivo and fully protects mice against fas-mediated fulminant liver destruction and death", Journal of Experimental Medicine,184, 2067-2072, (1996).
Grobmyer et al., "Peptidomimetic fluoromethylketone rescues mice from lethal endotoxic shock [In Process Citation]", 5, 585, (1999).
JJ Plattner et al., "Obstacles to Drug Development from Peptide Leads", Drug Discovery Technologies, 93-126, (1990).
Roland Dolle et al., "First Examples of Peptidomimetic Inhibitors of Interleukin-1β Converting Enzyme", Journal of Med. Chem., 39, 2438-2440, (1996).
Pierre Golstein, "Cell Death in Us and Others", Science, 281, 1283-1284, (1998).
Matthias Endres et al., "Attenuation of delayed neuronal death after mild focal ischemia in mice by inhibition of the caspase family", 18, 238-247, (1998).
Julian M.C. Golec et al., "Structure-based design of non-peptidic pyridone aldehydes as inhibitors of interleukin-1β converting enzyme", 7, 2181-2186, (1997).

* cited by examiner

Primary Examiner — Patricia Morris
(74) Attorney, Agent, or Firm — Jennifer G. Che

(57) ABSTRACT

The present invention provides a compound of formula I:

wherein $R^1$, $R^2$, $R^3$, $R^4$, and $R^5$ are as defined herein. The present invention also provides pharmaceutical compositions and methods using such compositions for treating a caspase-mediated diseases and processes for preparing the compounds of the invention.

26 Claims, No Drawings

CASPASE INHIBITORS AND USES THEREOF

CROSS REFERENCE TO RELATED APPLICATIONS

This present application claims the benefit, under 35 U.S.C. §119, to U.S. Provisional Application No. 60/630,926 filed on Nov. 24, 2004; the entire disclosure of which is incorporated herein by reference.

FIELD OF THE INVENTION

This invention is in the field of medicinal chemistry and relates to compounds, and pharmaceutical compositions thereof, that inhibit caspases that mediate cell apoptosis and inflammation. The invention also relates to processes for preparing these compounds. The invention further relates to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science*, 1998, 281, 1283-1312; Ellis et al., *Ann. Rev. Cell. Biol.*, 1991, 7, 663).

Caspases are a family of cysteine protease enzymes that are key mediators in the signaling pathways for apoptosis and cell disassembly (Thornberry, *Chem. Biol.*, 1998, 5, R97-R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, 5 and 13, have been shown to prefer hydrophobic aromatic amino acids at position 4 on the N-terminal side of the cleavage site. Another group which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their perceived function. The first subfamily consists of caspases-1 (ICE), 4, 5 and 13. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon-γ inducing factor (IGIF, also known as IL-18) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector capsases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

Knowledge of the four amino acid sequence primarily recognized by the caspases has been used to design caspase inhibitors. Reversible tetrapeptide inhibitors have been prepared having the structure $CH_3CO$—[P4]-[P3]-[P2]-CH(R) $CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149-155 (1997); Mjalli, et al., *Bioorg. Med. Chem. Lett.* 3, 2689-2692 (1993); Nicholson et al., *Nature* 376, 37-43 (1995). Irreversible inhibitors based on the analogous tetrapeptide recognition sequence have been prepared.

The utility of caspase inhibitors to treat a variety of mammalian disease states associated with an increase in cellular apoptosis has been demonstrated using peptidic caspase inhibitors. For example, in rodent models caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improved survival after endotoxic shock. Yaoita et al., *Circulation*, 97, 276 (1998); Endres et al., *J Cerebral Blood Flow and Metabolism*, 18, 238, (1998); Cheng et al., *J. Clin. Invest.*, 101, 1992 (1998); Yakovlev et al., *J Neuroscience*, 17, 7415 (1997); Rodriquez et al., *J. Exp. Med.*, 184, 2067 (1996); Grobmyer et al., *Mol. Med.*, 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies*, Clark and Moos, Eds. (Ellis Horwood, Chichester, England, 1990).

Recognizing the need to improve the pharmacological properties of the peptidic caspase inhibitors, peptidomimetic inhibitors have been reported. Amongst these, inhibitors where the P3 amino acid has been replaced by derivatives of 3-aminopyridin-2-ones and 5-aminopyrimidin-4-ones have been reported (U.S. Pat. No. 5,756,466 (Bemis et al.); PCT Publication No. WO 95/35308 (Bemis et al.); Dolle et al. *J.*

Med. Chem. 39, 2438, (1996); Golec et al. Bioorg. Med. Chem. Lett. 7, 2181, (1997); Semple et al, Biorg. Med. Chem. Lett. 7, 1337, (1997)).

Due to the inherent problems of the peptidic inhibitors, there continues to be a need for small molecule, nonpeptide caspase inhibitors that are potent, stable, and penetrate membranes to provide effective inhibition of apoptosis in vivo. Such compounds would be extremely useful in treating the aforementioned diseases where caspase enzymes play a role.

SUMMARY OF THE INVENTION

The present invention provides a compound of formula I:

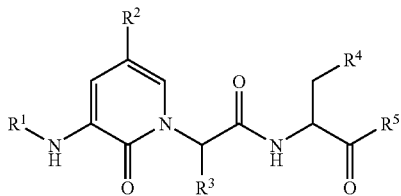

I wherein: $R^1$, $R^2$, $R^3$, $R^4$, and $R^5$ are as defined herein.

The present invention also provides pharmaceutical compositions comprising a compound of formula I and methods of using such compounds and compositions for treating caspase-mediated diseases. The present invention also provides processes for preparing the compounds of formula I.

DETAILED DESCRIPTION OF THE INVENTION

The present invention provides a compound of formula I:

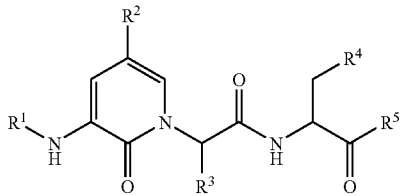

I wherein:
$R^1$ is $R^6C(O)-$, $HC(O)-$, $R^6SO_2-$, $R^6OC(O)-$, $(R^6)_2NC(O)-$, $(R^6)(H)NC(O)-$, $R^6C(O)C(O)-$, $(R^6)_2NC(O)C(O)-$, $(R^6)(H)NC(O)C(O)-$, or $R^6OC(O)C(O)-$;

$R^2$ is hydrogen, $-CF_3$, halo, $-OR^7$, $NO_2$, $-OCF_3$, $-CN$, or $R^8$;

$R^3$ is -T-$R^9$;

$R^4$ is $-COOH$ or $-COOR^8$;

$R^5$ is $-CH_2F$ or $-CH_2O-2,3,5,6$-tetrafluorophenyl;

$R^6$ is $R^{6a}$ or $R^{6b}$; two $R^6$ groups, together with the same atom to which they are bound, optionally form a 3- to 10-membered aromatic or nonaromatic ring; wherein the ring is optionally fused to a (C6-C10)aryl, (C5-C10)heteroaryl, (C3-C10)cycloalkyl, or a (C3-C10)heterocyclyl; wherein up to 3 aliphatic carbon atoms may be replaced by a group selected from O, N, N($R^7$), S, SO, and $SO_2$; and wherein each $R^6$ is independently substituted with up to 6 substituents independently selected from R;

$R^{6a}$ and $R^{6b}$ are each independently
  (C1-C3)-aliphatic-,
  (C4-C12)-aliphatic-,
  (C3-C10)-cycloaliphatic-,
  (C6-C10)-aryl-,
  (C3-C10)-heterocyclyl-,
  (C5-C10)-heteroaryl-,
  (C3-C10)-cycloaliphatic-(C1-C12)-aliphatic-,
  (C6-C10)-aryl-(C1-C12)-aliphatic-,
  (C3-C10)-heterocyclyl-(C1-C12)-aliphatic-,
  (C5-C10)-heteroaryl(C1-C12)-aliphatic-;

R is halogen, $-OR^7$, $-OC(O)N(R^7)_2$, $-NO_2$, $-CN$, $-CF_3$, $-OCF_3$, $-R^7$, oxo, thioxo, $=NR^7$, $=N(OR^7)$, 1,2-methylenedioxy, 1,2-ethylenedioxy, $-N(R^7)_2$, $-SR^7$, $-SOR^7$, $-SO_2R^7$, $-SO_2N(R^7)_2$, $-SO_3R^7$, $-C(O)R^7$, $-C(O)C(O)R^7$, $-C(O)C(O)OR^7$, $-C(O)C(O)N(R^7)_2$, $-C(O)CH_2C(O)R^7$, $-C(S)R^7$, $-C(S)OR^7$, $-C(O)OR^7$, $-OC(O)R^7$, $-C(O)N(R^7)_2$, $-OC(O)N(R^7)_2$, $-C(S)N(R^7)_2$, $-(CH_2)_{0-2}NHC(O)R^7$, $-N(R^7)N(R^7)COR^7$, $-N(R^7)N(R^7)C(O)OR^7$, $-N(R^7)N(R^7)CON(R^7)_2$, $-N(R^7)SO_2R^7$, $-N(R^7)SO_2N(R^7)_2$, $-N(R^7)C(O)OR^7$, $-N(R^7)C(O)R^7$, $-N(R^7)C(S)R^7$, $-N(R^7)C(O)N(R^7)_2$, $-N(R^7)C(S)N(R^7)_2$, $-N(COR^7)COR^7$, $-N(OR^7)R^7$, $-C(=NR^7)N(R^7)_2$, $-C(O)N(OR^7)R^7$, $-C(=NOR^7)R^7$, $-OP(O)(OR^7)_2$, $-P(O)(R^7)_2$, $-P(O)(OR^7)_2$, or $-P(O)(H)(OR^7)$;

two $R^7$ groups together with the atoms to which they are bound optionally form a 3- to 10-membered aromatic or non-aromatic ring having up to 3 heteroatoms independently selected from N, N($R^7$), O, S, SO, or $SO_2$, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from $J_2$; or each $R^7$ is independently selected from:
  hydrogen-,
  (C1-C12)-aliphatic-,
  (C3-C10)-cycloaliphatic-,
  (C3-C10)-cycloaliphatic-(C1-C12)-aliphatic-,
  (C6-C10)-aryl-,
  (C6-C10)-aryl-(C1-C12)aliphatic-,
  (C3-C10)-heterocyclyl-,
  (C6-C10)-heterocyclyl-(C1-C12)aliphatic-,
  (C5-C10)-heteroaryl-, or
  (C5-C10)-heteroaryl-(C1-C12)-aliphatic-; wherein $R^7$ has up to 3 substituents selected independently from $J_2$; and $J_2$ is halogen, $-OR^7$, $-OC(O)N(R^7)_2$, $-NO_2$, $-CN$, $-CF_3$, $-OCF_3$, $-R^7$, oxo, thioxo, $=NR^7$, $=NOR^7$, 1,2-methylenedioxy, 1,2-ethylenedioxy, $-N(R^7)_2$, $-SR^7$, $-SOR^7$, $-SO_2R^7$, $-SO_2N(R^7)_2$, $-SO_3R^7$, $-C(O)R^7$, $-C(O)C(O)R^7$, $-C(O)C(O)OR^7$, $-C(O)C(O)N(R^7)_2$, $-C(O)CH_2C(O)R^7$, $-C(S)R^7$, $-C(S)OR^7$, $-C(O)OR^7$, $-OC(O)R^7$, $-C(O)N(R^7)_2$, $-OC(O)N(R^7)_2$, $-C(S)N(R^7)_2$, $-(CH_2)_{0-2}NHC(O)R^7$, $-N(R^7)N(R^7)COR^7$, $-N(R^7)N(R^7)C(O)OR^7$, $-N(R^7)N(R^7)CON(R^7)_2$, $-N(R^7)SO_2R^7$, $-N(R^7)SO_2N(R^7)_2$, $-N(R^7)C(O)OR^7$, $-N(R^7)C(O)R^7$, $-N(R^7)C(S)R^7$, $-N(R^7)C(O)N(R^7)_2$, $-N(R^7)C(S)N(R^7)_2$, $-N(COR^7)COR_7$, $-N(OR^7)R^7$, $-CN$, $-C(=NR^7)N(R^7)_2$, $-C(O)N(OR^7)R^7$, $-C(=NOR^7)R^7$, $-OP(O)(OR^7)_2$, $-P(O)(R^7)_2$, $-P(O)(OR^7)_2$, or $-P(O)(H)(OR^7)$; and $R^8$ is
  (C1-C12)-aliphatic-,
  (C3-C10)-cycloaliphatic-, (C6-C10)-aryl-,
(C3-C10)-heterocyclyl-,
(C5-C10)-heteroaryl-,
(C3-C10)-cycloaliphatic-(C1-C12)-aliphatic-,
(C6-C10)-aryl-(C1-C12)-aliphatic-,
(C3-C10)-heterocyclyl-(C1-C12)-aliphatic-, or
(C5-C10)-heteroaryl-(C1-C12)-aliphatic-, wherein up to 3 aliphatic carbon atoms may be replaced with a group selected from O, N, N($R^7$), S, SO, and $SO_2$; and wherein $R^8$ is optionally substituted with up to 6 substituents independently selected from R.

T is a direct bond or (C1-C6) aliphatic wherein up to 2 aliphatic carbon atoms in T may be optionally replaced with S, —SO—, $SO_2$, O, N($R^7$), or N in a chemically stable arrangement; wherein each T may be optionally substituted with up to 3 R substituents;

$R^9$ is optionally substituted (C6-C10)-aryl or (C5-C10)-heteroaryl;

According to one embodiment of this invention, $R^1$ is $R^6C(O)$—, $(R^6)_2NC(O)$—, $R^6C(O)C(O)$—, $(R^6)_2NC(O)C(O)$—, $(R^6)(H)NC(O)C(O)$—, or $R^6OC(O)C(O)$—. In some embodiments, $R^6$ is $R^{6a}$. In other embodiments, $R^6$ is $R^{6b}$.

According to another embodiment $R^1$ is HC(O)—, $R^6SO_2$—, $R^6OC(O)$—, or $(R^6)(H)NC(O)$—. In some embodiments $R^6$ is $R^{6a}$. In other embodiments, $R^6$ is $R^{6b}$.

According to another embodiment $R^1$ is $R^6C(O)$— or $R^6SO_2$—. In another embodiment, $R^1$ is $R^6C(O)$—. In another embodiment, $R^1$ is $R^6SO_2$—.

According to another embodiment of this invention $R^1$ is $(R^6)_2NC(O)$—, $(R^6)(H)NC(O)$—, or $(R^6)OC(O)$—. In a preferred embodiment, $R^1$ is $(R^6)_2NC(O)$—. In another preferred embodiment, $R^1$ is $(R^6)(H)NC(O)$—. In yet another preferred embodiment, $R^1$ is $(R^6)OC(O)$—.

According to one embodiment of this invention, $R^6$ is $R^{6a}$. According to another embodiment, $R^6$ is $R^{6b}$. According to a third embodiment, $R^6$ is $R^{6a}$ or $R^{6b}$.

In one embodiment of this invention,
$R^{6a}$ is
(C4-C12)-aliphatic-,
(C3-C10)-cycloaliphatic-,
(C6-C10)-aryl-,
(C3-C10)-heterocyclyl-,
(C5-C10)-heteroaryl-,
(C3-C10)-cycloaliphatic-(C1-C12)-aliphatic-,
(C6-C10)-aryl-(C1-C12)-aliphatic-,
(C3-C10)-heterocyclyl-(C1-C12)-aliphatic-,
(C5-C10)-heteroaryl(C1-C12)-aliphatic-, or two $R^{6a}$ groups, together with the atom to which they are attached, optionally form a 3- to 10-membered aromatic or nonaromatic ring; wherein the ring is optionally fused to a (C6-C10)aryl, (C5-C10)heteroaryl, (C3-C10)cycloalkyl, or a (C3-C10)heterocyclyl; wherein up to 3 aliphatic carbon atoms may be replaced by a group selected from O, N, N($R^7$), S, SO, and $SO_2$; and wherein $R^{6a}$ is substituted with up to 6 substituents independently selected from R;

$R^{6b}$ is $R^{6a}$ or (C1-C3)-aliphatic-.

In another embodiment of this invention, $R^{6a}$ is
(C1-C4)-aliphatic,
(C3-C10)-cycloaliphatic,
(C3-C10)-heterocyclyl,
(C5-C10)-heteroaryl,
(C6-C10)-aryl-, or
(C6-C10)-aryl-(C1-C12)-aliphatic (it being understood that optionally up to 3 aliphatic carbon atoms may be replaced by a group selected from O, N, N($R^7$), S, SO, and $SO_2$; and wherein $R^{6a}$ is optionally substituted with up to 6 substituents independently selected from R; or $R^{6a}$ is substituted as disclosed in any of the embodiments herein).

In another embodiment, each $R^{6a}$ is independently
(C4)-aliphatic,
(C3-C10)-cycloaliphatic,
(C3-C10)-heterocyclyl,
(C5-C10)-heteroaryl,
(C6-C10)-aryl-, or
(C6-C10)-aryl-(C1-C12)-aliphatic (it being understood that optionally up to 3 aliphatic carbon atoms may be replaced by a group selected from O, N, N($R^7$), S, SO, and $SO_2$; and wherein $R^{6a}$ is optionally substituted with up to 6 substituents independently selected from R; or $R^{6a}$ is substituted as disclosed in any of the embodiments herein).

In one embodiment, each $R^{6a}$ is independently (C4)-aliphatic-, (C3-C7)-cycloaliphatic, (C6-C10)-aryl-, or (C5-C10)-heteroaryl; wherein the heteroaryl and aryl are independently and optionally substituted, or each $R^6$ together with the N-atom to which it is attached is a (C3-C7)-cycloaliphatic;

According to another embodiment, each $R^{6a}$ is independently (C3-C7)-cycloaliphatic, (C6-C10)-aryl-, or (C5-C10)-heteroaryl, wherein the heteroaryl and aryl are independently and optionally substituted, or each $R^6$ together with the N-atom to which it is attached is a (C3-C7)-cycloaliphatic.

In another embodiment, each $R^{6a}$ is independently (C4)-aliphatic-, (C5-C10)-heteroaryl-, or (C6-C10)-aryl-; wherein the heteroaryl or aryl is optionally substituted or wherein two $R^{6a}$ groups together with the N-atom to which they are attached form a (C3-C7)-cycloaliphatic group; in a preferred embodiment each $R^{6a}$ is independently (C5-C10)-heteroaryl- or (C6-C10)-aryl-.

In another embodiment, each $R^{6a}$ is independently H, (C4)-aliphatic-, or (C6-C10)-aryl-; In a preferred embodiment each $R^{6a}$ is (C6-C10)-aryl-; or each $R^{6a}$, together with the N-atom to which it is attached, is a (C3-C7)-cycloaliphatic;

In another embodiment, each $R^{6a}$ is independently (C4)-aliphatic- or (C6-C10)-aryl-; wherein the aryl is optionally substituted or wherein two $R^6$ groups, together with the N-atom to which they are attached, form a (C3-C7)-cycloaliphatic; In another embodiment, each $R^{6a}$ is independently (C6-C10)-aryl-.

According to certain embodiments, each $R^{6b}$ is independently $R^{6a}$ or (C1-C3)-aliphatic-.

According to one embodiment of this invention, $R^2$ is hydrogen, C1-, C2-, C3-, or C4-alkyl-, —$CF_3$, —Cl, —$OR^7$, —$NO_2$, —$OCF_3$, or —CN. More preferably, $R^2$ is hydrogen, C1-alkyl-, C2-alkyl-, or $CF_3$. More preferably, $R^2$ is hydrogen or $CF_3$.

According to one embodiment, T is (C1-C4) aliphatic wherein up to one aliphatic carbon atom may be replaced with a group selected from O, N, N($R^7$), and S.

According to another embodiment, T is (C1-C4) aliphatic wherein zero aliphatic carbons atom are replaced with a group selected from O, N, N($R^7$), and S.

In yet another embodiment, T is a direct bond, —$CH_2$—, —CH(Me)—, —$CH_2$—$CH_2$—, —$CH_2$—O—$CH_2$—, —CH(Me)—O—$CH_2$—, or —$CH_2$—$CH_2$—O—$CH_2$—.

In one embodiment T is —$CH_2$— or —$CH_2$—$CH_2$—; In another embodiment T is —$CH_2$—.

According to another embodiment, $R^9$ is optionally substituted C6 aryl or C5-heteroaryl.

According to one embodiment, $R^9$ is substituted phenyl. Examples of preferred phenyl substituents for $R^9$ include halogen, —$OR^7$, —$NO_2$, —$CF_3$, —$OCF_3$, —$R^7$, —O-benzyl, —O-phenyl, 1,2-methylenedioxy, 1,2-ethylenedioxy, —N($R^7$)$_2$, —C(O)$R^7$, —COO$R^7$ and —CON($R^7$)$_2$ wherein $R^7$ is defined as above.

According to another embodiment, $R^9$ is unsubstituted phenyl.

According to one embodiment, $R^5$ is —CH$_2$O-2,3,5,6-tetrafluorophenyl.

According to another embodiment, $R^5$ is —CH$_2$F.

According to another embodiment, $R^8$ is (C1-C12)-alkyl. More preferably, $R^8$ is (C1-C4)-alkyl.

According to a preferred embodiment, each R and $J_2$ are independently halogen, —O$R^7$, —OC(O)N($R^7$)$_2$, —N$_2$, —CN, —CF$_3$, —OCF$_3$, —$R^7$, oxo, 1,2-methylenedioxy, 1,2-ethylenedioxy, —N($R^7$)$_2$, —C(O)$R^7$, —C(O)C(O)$R^7$, —C(O)O$R^7$, —OC(O)$R^7$, —C(O)N($R^7$)$_2$, or —OC(O)N($R^7$)$_2$.

As used herein, the carbon atom designations may have the indicated integer and any intervening integer. For example, the number of carbon atoms in a (C1-C4)-alkyl group is 1, 2, 3, or 4. It should be understood that these designation refer to the total number of atoms in the appropriate group. For example, in a (C3-C10)-heterocyclyl the total number of carbon atoms and heteroatoms is 3 (as in aziridine), 4, 5, 6 (as in morpholine), 7, 8, 9, or 10.

As used herein, an aliphatic group includes straight-chained and branched groups having the specified number of atoms. If the number of atoms is unspecified, the aliphatic group has from 1 to 12 carbon atoms. As would be understood, alkenyl and/or alkynyl aliphatic groups have a minimum of 2 carbon atoms. Preferred aliphatic groups are alkyl groups (preferably having from 1 to 6 atoms).

Accordingly, unless otherwise specified, preferred aliphatic groups of this invention are alkyl groups and have 1, 2, 3, 4, 5, or 6 carbon atoms. More preferred alkyl groups have 1, 2, 3, or 4 carbon atoms. Preferred alkenyl and alkynyl groups of this invention have 2, 3, 4, 5, or, 6 carbon atoms and more preferably, from 2, 3, or 4 carbon atoms.

Cycloalkyl and cycloalkenyl groups have between 3 and 10 carbon atoms and are monocyclic or bicyclic, including linearly fused, bridged, or spirocyclic. A cycloaliphatic group is, preferably, a cycloalkyl or a cylcoalkenyl. More preferred cycloaliphatic groups are 3-, 4-, 5-, 6-, or 7-membered rings that are, more preferably, cycloalkyl rings.

As used herein, "aromatic group" or "aryl" refers to a 6-10-membered ring system that contains at least one aromatic ring. Example of aromatic rings include phenyl and naphthyl.

As used herein a "heteroaryl" refers to ring system having 5-10 members and 1, 2, or 3 heteroatoms independently selected from N, N($R^7$), O, S, SO, and SO$_2$, wherein at least one ring is heteroaromatic (e.g., pyridyl, thiophene, or thiazole). Preferred heteroaryl groups are 5- or 6-membered rings having 1 or 2 heteroatoms. In certain embodiments of this invention, more preferred heteroaryl groups are those that have contain a "=N" group.

Examples of heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein a "heterocycle" refers to ring system having 3-10 members and 1, 2, or 3 heteroatoms independently selected from N, N($R^7$), O, S, SO, and SO$_2$, wherein no ring is aromatic (e.g., piperidine and morpholine). Preferred heterocyclyl groups are 5- or 6-membered rings having 1 or 2 heteroatoms.

Examples of heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Any of these cycloaliphatic, heterocyclyl, and heteroaryl groups are optionally fused with a 5- or 6-membered aryl or heteroaryl ring. Furthermore, each of any aliphatic, aryl, cycloaliphatic, heteroaryl, and heterocyclyl may contain appropriate substituents (preferably up to 5, more preferable up to 3, and even more preferably, 0 or 1) independently selected from, for example, carbonyl and R. Preferred substituents (including R and $J_2$) are halogen, —O$R^7$, —NO$_2$, —CF$_3$, —OCF$_3$, —$R^7$, oxo, —O$R^7$, —O-benzyl, —O-phenyl, 1,2-methylenedioxy, 1,2-ethylenedioxy, —N($R^7$)$_2$, —C(O)$R^7$, —COO$R^7$ or —CON($R^7$)$_2$, wherein $R^7$ is defined herein (and is preferably H, (C1-C6)-alkyl, or (C2-C6)-alkenyl and alkynyl), with (C1-C6)-alkyl being most preferred). It should be understood that this definition would include a perfluorinated alkyl group.

In embodiments of this invention where R is a substituent on a nitrogen atom, preferred R groups are selected from the group consisting of —$R^7$, —SO$R^7$, —SO$_2$$R^7$, —SO$_2$N($R^7$)$_2$, —SO$_3$$R^7$, —C(O)$R^7$, —C(O)C(O)$R^7$, —C(O)C(O)O$R^7$, —C(O)C(O)N($R^7$)$_2$, —C(O)CH$_2$C(O)$R^7$, —C(S)$R^7$, —C(S)O$R^7$, —C(O)O$R^7$, —C(O)N($R^7$)$_2$, —C(S)N($R^7$)$_2$, —(CH$_2$)$_{0-2}$NHC(O)$R^7$, —N($R^7$)N($R^7$)COR$^7$, —N($R^7$)N($R^7$)C(O)O$R^7$, —N($R^7$)N($R^7$)CON($R^7$)$_2$, —N($R^7$)SO$_2$$R^7$, —N($R^7$)SO$_2$N($R^7$)$_2$, —N($R^7$)C(O)O$R^7$, —N($R^7$)C(O)$R^7$, —N($R^7$)C(S)$R^7$, —N($R^7$)C(O)N($R^7$)$_2$, —N($R^7$)C(S)N($R^7$)$_2$, —N(COR$^7$)COR$^7$, —N(OR$^7$)$R^7$, —C(=NR$^7$)N($R^7$)$_2$, —C(O)N(OR$^7$)$R^7$, —C(=NOR$^7$)$R^7$, —OP(O)(OR$^7$)$_2$, —P(O)($R^7$)$_2$, —P(O)(OR$^7$)$_2$, and —P(O)(H)(OR$^7$), wherein $R^7$ is defined herein (and is preferably H, (C1-C6)-alkyl, or (C2-C6)-alkenyl and alkynyl), with (C1-C6)-alkyl being most preferred). More preferably, such R groups are selected from the group consisting of —$R^7$ and —C(O)$R^7$.

It should be understood that as small molecule, nonpeptide caspase inhibitors, the compounds of this invention would have a reasonable number of substituents, particularly in the variables that are themselves substituents. Accordingly, if a first $R^7$ group comprises a $J_2$ substituent that comprises a second $R^7$ group, the second $R^7$ group would preferably not be substituted with another $J_2$ group.

In preferred compounds of this invention, the stereochemistry is as depicted below:

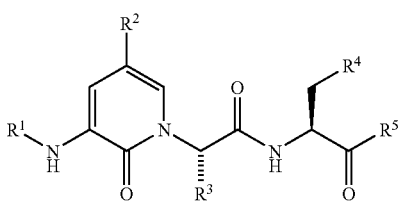

Any of the embodiments disclosed herein may be combined to provide alternative embodiments of this invention. Specific embodiments of this invention may be selected from the substituents depicted in the compounds of Table 1.

The compounds of the present invention are broad caspase inhibitors and have an improved ability over reported compounds to inhibit apoptosis.

According to one embodiment, this invention provides a compound of formula Ia or Ib:

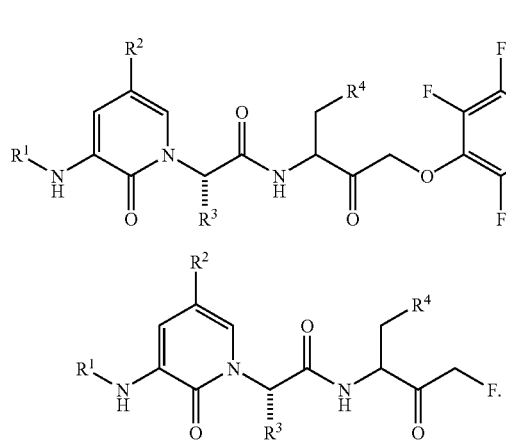

According to another embodiment, this invention provides a compound of formula Ic or Id:

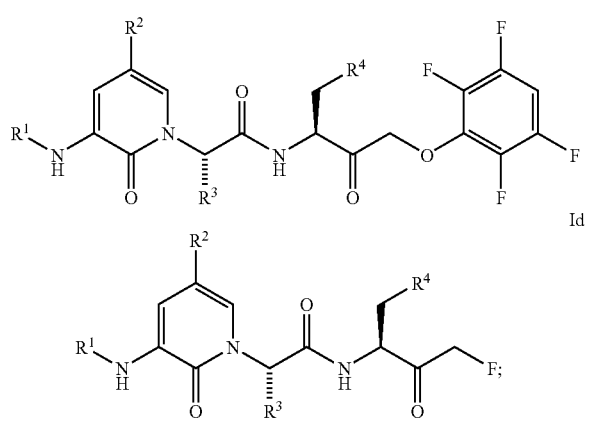

wherein $R^1$, $R^2$, $R^3$, and $R^4$ are as defined in any of the embodiments herein.

According to a more preferred embodiment, this invention provides a compound of formula II, selected from Table 1 below:

TABLE 1

Compounds of the invention.
In the table below, the following definitions are used:
"Ph" is phenyl, "Bn" is benzyl [—CH$_2$—Ph], "Et" is ethyl [—CH$_2$—CH$_3$], and "I—Pr" is isopropyl [—CH(CH$_3$)$_2$].

II

| Ex. | $R^1$ | $R^2$ | $R^3$ | $R^5$ |
|---|---|---|---|---|
| II.1 | Ph(C=O)— | H | Bn | CH$_2$F |
| II.2 | Ph(C=O)— | H | CH$_2$CH$_2$Ph | CH$_2$F |
| II.3 | Ph(C=O)— | CH$_3$ | Bn | CH$_2$F |
| II.4 | 2,6 dimethylphenyl(C=O)— | H | Bn | CH$_2$F |
| II.5 | 2,6 dichlorophenyl(C=O)— | H | Bn | CH$_2$F |
| II.6 | (Et)$_2$N(C=O)— | H | Bn | CH$_2$F |
| II.7 | Bn(C=O)— | H | Bn | CH$_2$F |
| II.8 | 2,6 dichlorophenyl(C=O)— | H | Bn | CH$_2$O-2,3,4,5-tetra fluoro phenyl |
| II.9 | PhNH(C=O)— | H | Bn | CH$_2$F |
| II.10 | Ph(C=O) | CF$_3$ | Bn | CH$_2$F |
| II.11 | i-Pr(C=O)— | H | Bn | CH$_2$F |
| II.12 | Ph(C=O)— | H | 3-thienyl methyl | CH$_2$F |
| II.13 | Et(C=O)— | H | Bn | CH$_2$F |
| II.14 | Ph(C=O)— | H | 2-thienyl methyl | CH$_2$F |
| II.15 | Ph(C=O)— | H | 3-indolyl methyl | CH$_2$F |
| II.16 | Et(SO2)— | H | Bn | CH$_2$F |
| II.17 | Et(C=O)— | H | (CH)$_2$—OBn | CH$_2$F |
| II.18 | Et(C=O)— | H | CH(Me)—OBn | CH$_2$F |
| II.19 | Et(C=O)— | H | Ph | CH$_2$F |
| II.20 | Et(C=O)— | H | CH$_2$OBn | CH$_2$F |

According to another embodiment, the present invention provides a pharmaceutical composition comprising:

a) a compound of formula I, as defined herein, or a pharmaceutically acceptable salt thereof; and b) a pharmaceutically acceptable carrier, adjuvant or vehicle.

It will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

The compounds of this invention may be prepared in general by methods known to those skilled in the art for analogous compounds and by the preparative examples that follow. See, for example, WO 2004/106304, which is incorporated herein by reference. For the purposes of illustration, the following Schemes I-III for the synthesis of the compounds of the present invention are provided. It should be understood that any protective group depicted in the schemes may be varied as appropriate in view of compatibility with other substituents.

Various protecting groups may be used in the methods of this invention (see, e.g., T. W. Greene & P. G. M Wutz, "Protective Groups in Organic Synthesis", 3rd Edition, John Wiley & Sons, Inc. (1999) and the earlier editions of this book). Typical functional groups that must be protected are amines. Any amines and other functional groups may be protected according to methods known in the art. Compounds, including amines, may be used with or without isolation from the reaction mixtures.

Scheme I

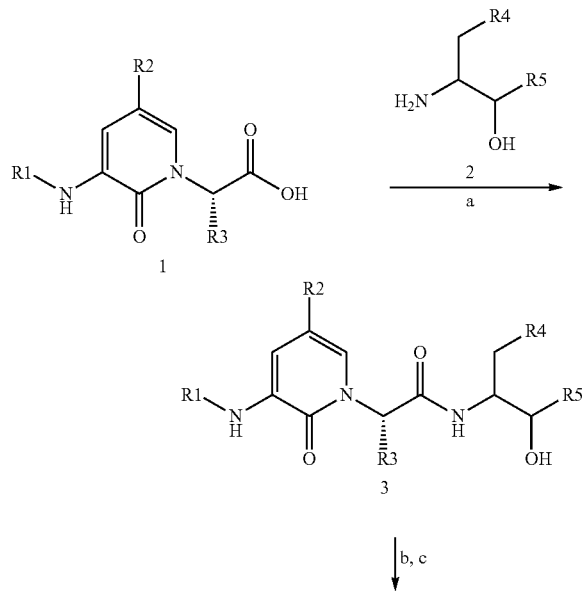

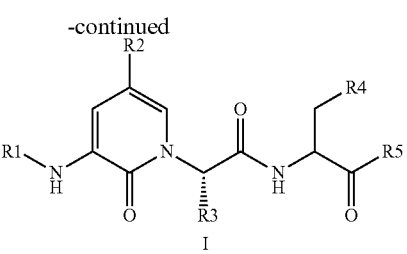

Scheme I (a) EDC/DMAP/HOBt/THF; (b) Dess-Martin periodinane; (c) TFA/DCM

In Scheme I above, the following abbreviations are used: EDC is 1-(3-dimethylaminopropyl)-3-ethylcarbodiimide; HOBt is 1-hydroxybenzotriazole; THF is tetrahydrofuran; TFA is trifluoroacetic acid; DCM is dichloromethane; DMAP is 4-dimethylaminopyridine. Acid 1 is coupled to amino alcohol 2. Here the coupling is depicted using EDC/DMAP/HOBt/THF, however, other suitable conditions may also be used. Depending on the nature of $R^4$ and $R^5$ an amino ketone may be used, in place of the amino alcohol, thus avoiding the subsequent oxidation step. In the case of fluoromethyl ketones where $R^5$ is $CH_2F$, the amino alcohol 2 may be obtained according to the method of Revesz et al., *Tetrahedron Lett.* 1994, 35, 9693. In the case of tetrafluorophenoxy ketones where $R^5$ is —$CH_2O$-2,3,5,6-tetrafluorophenyl, amino alcohol 2 may be obtained by methods analogous to those of Semple et al., *Bioorganic and Medicinal Chemistry Letters*, 1997, 7, 1337 (Scheme II).

Finally the hydroxy group in compound 3 is oxidized (e.g., with Dess-Martin periodinane) and the resulting compound treated appropriately according to the nature of $R^4$. For example, in product I if $R^4$ is a carboxylic acid, then $R^4$ in 3 is preferably an ester that is hydrolyzed in the final step of the scheme. If that ester is a t-butyl ester (i.e., if $R^4$ is $CO_2tBu$), treatment with trifluoroacetic acid will give the acid. The ester is preferably a t-butyl ester when the other substituents in I are compatible with acidic conditions.

If $R^4$ in product I is an ester, the desired ester may be prepared by esterifying the corresponding acid or by having the desired ester group already present in compound 2.

Scheme II

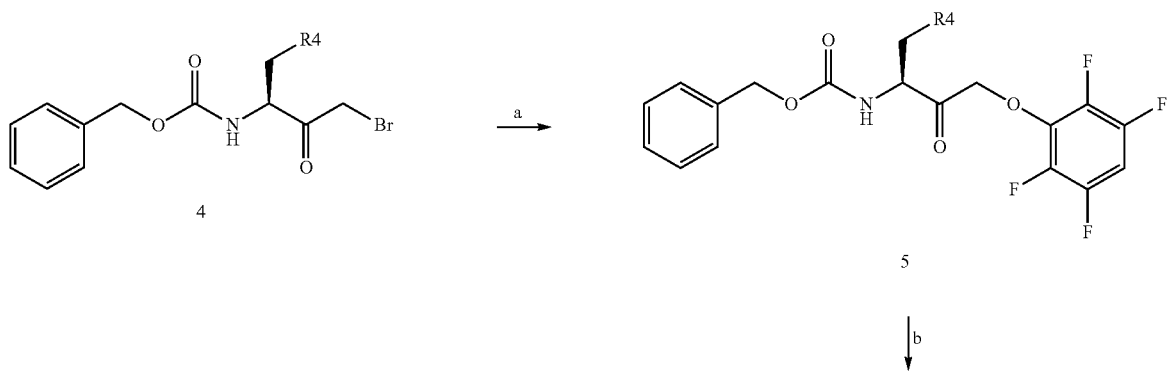

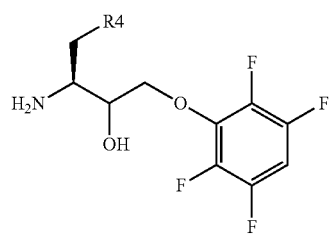
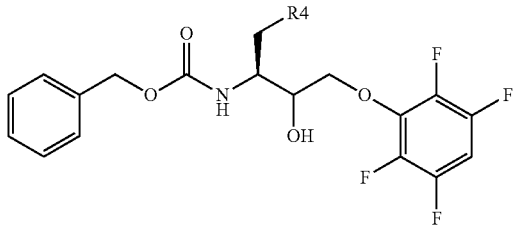

Scheme II (a) KF/DMF/ArOH; (b) NaBH₄/THF; (c) H₂/Pd/C/MeOH

In scheme II above, the following abbreviations are used: KF is potassium fluoride; DMF is N,N-dimethylformamide; ArOH is 2,3,5,6-tetrafluorophenol; THF is tetrahydrofuran; MeOH is methanol. Commercially available bromoketone 4 ($R^4$=CO₂tBu) is reacted with 2,3,5,6-tetrafluorophenol and potassium fluoride to give phenoxy ketone 5. The ketone is then reduced with a suitable reducing agent, for example, sodium borohydride, to give the alcohol 6, which is hydrogenated by using hydrogen gas and a suitable catalyst, for example, palladium on carbon, to give the amino alcohol 2 ($R^4$=CO₂tBu, $R^5$=CH₂O-2,3,5,6-tetrafluorophenyl).

done acid derivatives 1 can be prepared in chiral form using the synthetic sequence shown in Scheme III. Commercially available nitropyridone is reduced to the amine with hydrogen and palladium/carbon. The amino group is then functionalised with the appropriate electrophile: in the case of R1=Cbz the benzyloxycarbonyl protected amine is prepared using a procedure similar to that described by Warner et al *J. Med. Chem.* 1994, 37(19), 3090-3099. For the other cases the amine is derivatised using standard methods. (R)-tert-butyl-2-hydroxy ester is treated with trifluoromethanesulphonic anhydride and 2,6-lutidine in DCM to give the corresponding triflate. Reaction of the triflate with the anion of the function- Scheme III

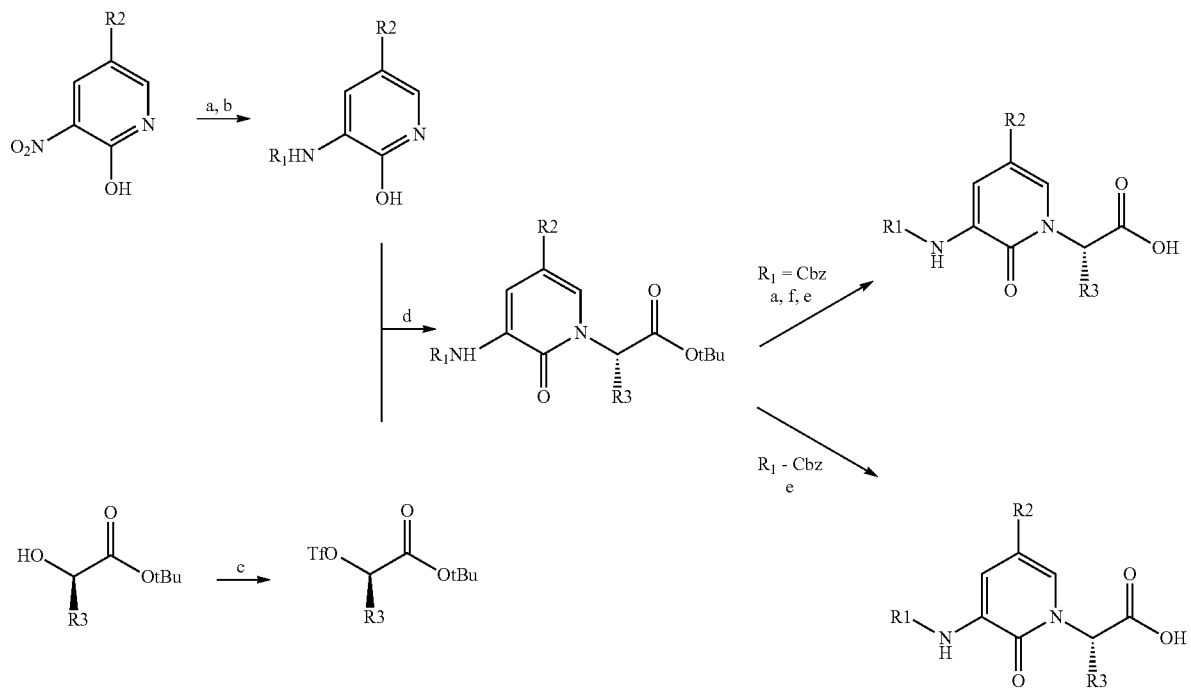

Scheme III (a) H₂ Pd/C MeOH; (b) R¹—Cl, Na₂CO₃, H₂O/THF;
(c) (CF₃SO₂)₂O, 2,6-Lutidine, DCM; (d) NaH, THF;
(e) TFA/DCM; (f) R¹—Cl, Et₃N, DMAP, DCM;

In Scheme III the folowing abreviatons are used: Cbz is a benzyloxycarbonyl protecting group; MeOH is methanol; DCM is dichloromethane; TFA is trifluoroacetic acid; DMAP is 4-dimethylaminopyridine; THF is tetrahydrofuran. Pyrialized 2-hydroxypyridine (prepared by deprotonation with sodium hydride in THF) gives the N-alkylated pyridone. When $R^1$ is a benzyloxycarbonyl protecting group it can be removed at this stage using hydrogen and palladium on carbon to give the amine; this is then reacted with an appropriate electrophile, triethylamine and DMAP in DCM. For example if $R^1$ is required to be $R^6C{=}O$ (an amide) then an appropriately substituted acid chloride may be used. If $R^1$ is required to be $R^6S({=}O)_2$ (sulphonamide) then an appropriately substituted sulfonyl chloride may be used. If $R^1$ is $(R6)_2N(C{=}O)$ (urea) then an appropriately substituted carbamoyl chloride or isocyanate may be used. The other $R^1$ groups may be prepared accordingly. Acid 1 is then prepared by deprotection of the ester by, for example, using trifluoroacetic acid. The acid is then coupled to amino alcohol 2 (Scheme 1).

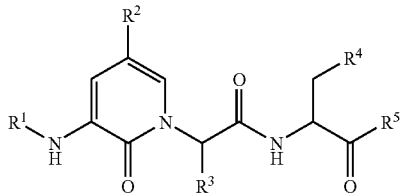

Scheme IV

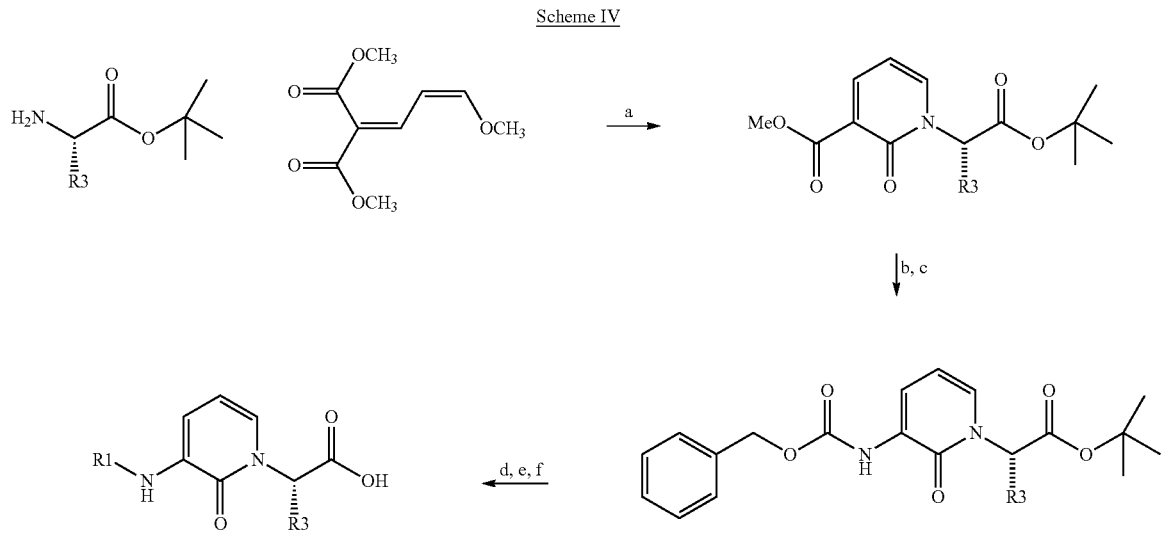

Scheme IV (a) NaOMe, MeOH; (b) LiOH/H$_2$O/dioxane; (c) DPPA, TEA, BnOH, dioxane; (d) H$_2$ Pd/C MeOH; (e) $R^1$—Cl, Et$_3$N, DMAP, DCM; (f) TFA/DCM;

In Scheme IV the folowing abbreviations are used: MeOH is methanol; DPPA is diphenylphosporyl azide; BnOH is benzyl alcohol; TEA is triethylamine; DCM is dichloromethane; TFA is trifluoroacetic acid; THF is tetrahydrofuran; Pyridone acids derivatives 1 can be prepared in chiral form using an alternative route, depicted in Scheme IV. Reaction of 2-(3-Methoxy-allylidene)-malonic acid dimethyl ester and aminoacid tert-butyl esters in the presence of methoxide gives the cyclised pyridone product. Hydrolysis of the methyl ester into the acid, followed by treatment of the acid under Curtius rearrangement conditions in the presence of benzyl alcohol give the benzyloxycarbonyl protected aminopyridone. The benzyloxycarbonyl protecting group is removed under hydrogenolysis conditions and the resulting amine is then reacted with an appropriate electrophile, triethylamine and DMAP in DCM. For example if $R^1$ is required to be $R^6C{=}O$ (an amide) then an appropriately substituted acid chloride may be used. If $R^1$ is required to be $R^6S({=}O)_2$ (sulphonamide) then an appropriately substituted sulfonyl chloride may be used. If $R^1$ is $(R^6)_2N(C{=}O)$ (urea) then an appropriately substituted carbamoyl chloride or isocyanate may be used. The other $R^1$ groups may be prepared accordingly. Acid 1 is then prepared by deprotection of the ester by, for example, using trifluoroacetic acid. The acid is then coupled to amino alcohol 2 (Scheme 1).

Therefore, another embodiment of this invention provides a process for preparing a compound of formula I:

wherein $R^1$, $R^2$, $R^3$, $R^4$, and $R^5$, are as defined in any of the embodiments herein, comprising:
(a) reacting a compound of formula (III):

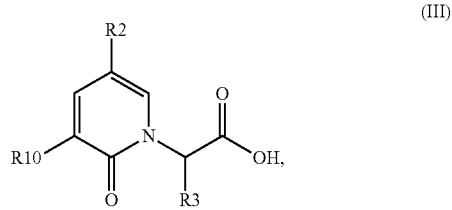

wherein:
$R^{10}$ is —NO$_2$, —C(O)OR$^{11}$, $R^6$C(O)N(H)—, $R^6$SO$_2$N(H)—, $R^6$OC(O)N(H)—, $(R^6)_2$NC(O)N(H)—, $R^6$C(O)C(O)N(H)—, $(R^6)_2$NC(O)C(O)N(H)—, or $R^6$OC(O)C(O)N(H)—;

$R^{11}$ is independently hydrogen, (C1-C12)-aliphatic-, (C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, (C5-C10)-heteroaryl(C1-C12)-aliphatic-, wherein up to 3 aliphatic carbon atoms may be replaced with a group selected from O, N(H), N(R$^7$), S, SO, and SO$_2$; and wherein $R^{11}$ is optionally substituted with up to 6 substituents independently selected from R; and R, $R^2$, $R^3$, and $R^6$ are as defined in any of the embodiments of formula (I) herein;
with a compound of formula (IV):

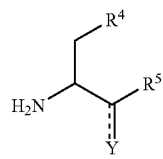

(IV)

wherein Y is either a carbonyl group or an OH group; and
$R^4$ and $R^5$ are as defined in any of the embodiments of formula (I) herein; in the presence of peptide coupling conditions and a solvent;
provided that if Y is an OH group, then the process further comprises (b) oxidizing the OH group to provide the compound of formula (I); and
provided that if $R^{10}$ is —$NO_2$, —C(O)$OR^{11}$, or —CN, the process comprises the further step of converting the —$NO_2$, —C(O)$OR^{11}$, or —CN into $R^6$C(O)N(H)—, $R^6SO_2$N(H)—, $R^6$OC(O)N(H)—, $(R^6)_2$NC(O)N(H)—, $R^6$C(O)C(O)N(H)—, $(R^6)_2$NC(O)C(O)N(H)—, or $R^6$OC(O)C(O)N(H)—.

The coupling conditions may be any known to skilled practitioners for forming peptidyl bonds. Preferred coupling conditions are EDC/DMAP/HOBt. A preferred solvent in the above embodiment is THF.

In a preferred embodiment, the compound of formula (III):

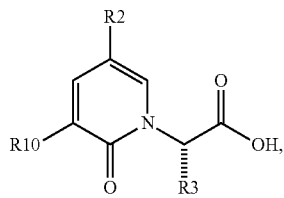

(III)

wherein $R^2$, $R^3$, and $R^9$ are as defined herein; is prepared by a process comprising:
(c) reacting a compound of formula (V):

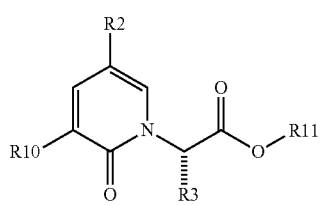

(V)

wherein R, $R^2$, $R^3$, and $R^{10}$ are as defined herein; in a solvent in the presence of deprotecting conditions.

The deprotecting conditions will depend on the specific protecting group (i.e., $R^{11}$). For example, if $R^{11}$ is t-butyl, then preferred deprotecting conditions would include acid hydrolysis. A preferred acid is TFA. A preferred solvent is DCM. More preferably the solvent and the hydrolyzing conditions comprise TFA and DCM. If $R^{11}$ is methyl or ethyl, then preferred deprotecting conditions would be basic (e.g., aqueous NaOH). If $R^{11}$ is benzyl, then the benzyl group could be removed by hydrogenolysis.

In a preferred embodiment, the compound of formula (V):

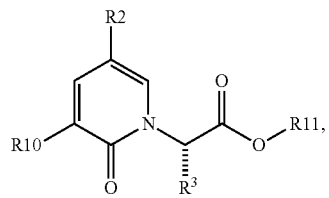

(V)

wherein $R^2$, $R^3$, $R^{10}$, and $R^{11}$ are as defined herein; is prepared by a process comprising:
(d) reacting a compound of formula (VI):

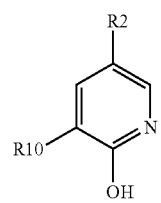

(VI)

wherein $R^2$ and $R^{10}$ are as defined herein; with a compound of formula (VII):

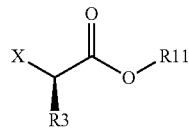

(VII)

wherein X is a suitable leaving group; and
$R^3$ and $R^{11}$ are as defined herein;
in the presence of a solvent and a base.

Preferably, X is —I, —Br, —Cl, —OH, an alkylsulfonate, or an aryl sulfonate. When X is —OH, an appropriate leaving group may be generated in situ (e.g., as in the Mitsunobu reaction). Preferred sulfonates include —O-trifluoromethanesulfonate, —O-methanesulfonate, —O-benzenesulfonate, —O-p-toluenesulfonate, —O-m-nitrobenzenesulfonate, and —O-p-nitrobenzenesulfonate. Suitable leaving groups useful in the methods of this invention are well known in the art. See, e.g., "March's Advanced Organic Chemistry", 5$^{th}$ Ed., Ed.: Smith, M. B. and March, J., John Wiley & Sons, New York (2001).

Any solvent that is compatible with the generation of anions may be used. Preferred solvents include DMF, toluene, and THF.

Suitable bases include any that may remove a proton from the hydroxy group in (V). Such bases include BuLi, LDA, LHMDS, and NaH. Preferably, the base is NaH.

Another embodiment of this invention provides a process for preparing a compound of formula (VIII):

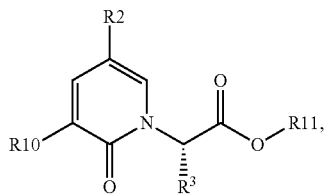

wherein:
R$^2$ is —CF$_3$, —Cl, —OR$^7$, —NO$_2$, —OCF$_3$, —CN, or R$^8$; and

R$^3$, R$^8$, R$^{10}$ and R$^{11}$ are as defined herein; comprising the step of (e) reacting a compound of formula (IX):

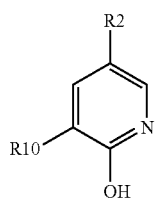

wherein R$^2$ and R$^{10}$ are as defined herein;
with a compound of formula (VII):

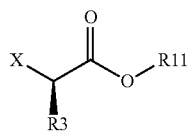

wherein R$^3$ and R$^{11}$ are as defined herein; and

X is a suitable leaving group; in the presence of a solvent and a base.

Preferably, X is —I, —Br, —Cl, —OH, an alkylsulfonate, or an aryl sulfonate. When X is —OH, an appropriate leaving group may be generated in situ (e.g., as in the Mitsunobu reaction). Preferred sulfonates include —O-trifluoromethanesulfonate, —O-methanesulfonate, —O-benzenesulfonate, —O-p-toluenesulfonate, —O-m-nitrobenzenesulfonate, and —O-p-nitrobenzenesulfonate.

Any solvent is compatible with the generation of anions may be used. Such solvents include DMF, toluene, and THF. Preferably, the solvent is THF.

Suitable bases include any that may remove a proton from the hydroxy group in (V). Such bases include BuLi, LDA, LHMDS, and NaH. Preferably, the base is NaH.

Another embodiment of this invention provides a process for preparing a compound of formula (I):

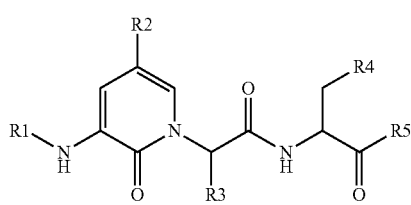

wherein R$^1$, R$^2$, R$^3$, R$^4$, and R$^5$, are as defined in any of the embodiments herein, comprising:

(a) reacting a compound of formula (VI or IX):

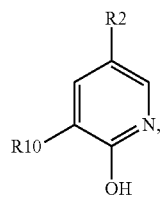

wherein:
R$^{10}$ is —NO$_2$, —C(O)OR$^{11}$, —CN, R$^6$C(O)N(H)—, R$^6$SO$_2$N(H)—, R$^6$OC(O)N(H)—, (R$^6$)$_2$NC(O)N(H)—, R$^6$C(O)C(O)N(H)—, (R$^6$)$_2$NC(O)C(O)N(H)—, or R$^6$OC(O)C(O)N(H)—; and R$^2$, R$^3$, and R$^6$ are as defined herein; with a compound of formula (X):

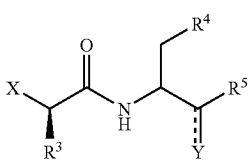

wherein Y is either a carbonyl group or an OH group; and R$^4$ and R$^5$ are as defined herein;

in the presence of any of the coupling conditions defined herein and a solvent;

provided that if Y is an OH group, then the process further comprises (b) oxidizing the OH group to provide the compound of formula (I); and provided that if R$^{10}$ is —NO$_2$, —C(O)OR$^{11}$, or —CN, the process comprises the further step of converting the —NO$_2$, —C(O)OR$^{11}$, or —CN into R$^{6b}$C(O)N(H)—, R$^{6a}$SO$_2$N(H)—, R$^{6b}$ OC(O)N(H)—, (R$^{6b}$)$_2$NC(O)N(H)—, R$^{6b}$C(O)C(O)N(H)—, (R$^{6b}$)$_2$NC(O)C(O)N(H)—, or R$^{6b}$OC(O)C(O)N(H)—.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides;

dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

For example, a carboxylic acid group in a compound of this invention may be derivatized as, for example, an ester. Preferred esters would be those derived from:

a $C_{1-6}$ straight-chained or branched alkyl, alkenyl, or alkynyl, wherein the alkyl, alkenyl, or alkynyl is optionally substituted with aryl, $CF_3$, Cl, F, OMe, OEt, $OCF_3$, CN, or $NMe_2$;

a $C_{1-6}$ cycloalkyl, wherein 1-2 carbon atoms in the cycloalkyl is optionally replaced with —O— or —$NR^9$—.

Compounds of this invention having a carbonyl group may be similarly derivatized as, e.g., an acetal, ketal, oxime (=$NOR^9$), hydrazine (=$NN(R^9)_2$), thioacetal, or thioketal.

Appropriate derivatives of amines are known in the art and are also included within the scope of this invention.

Certain of the above derivatives would include the protective groups known to skilled practitioners (see, e.g., T. W. Greene & P. G. M Wutz, "Protective Groups in Organic Synthesis", $3^{rd}$ Edition, John Wiley & Sons, Inc. (1999)). Typical functional groups that must be protected are amines. Any amines and other functional groups may be protected according to methods known in the art. Compounds, including amines, may be used with or without isolation from the reaction mixtures. As would be recognized by a skilled practitioner, these protective groups may also be employed in the processes of this invention.

Without being bound by theory, applicants' cyclic acetal compounds are believed to be prodrugs. That is, the acetal portion is cleaved in vivo to provide a corresponding acid-aldehyde compound. As would be recognized by a skilled practitioner, chemical compounds may be metabolized in vivo, e.g., at a site other than the prodrug cleavage site. Any such metabolites are included within the scope of this invention.

The compounds of this invention may be assayed for their ability to inhibit apoptosis, the release of IL-1β or caspase activity directly. Assays for each of the activities are known in the art. However, as would be recognized by a skilled practitioner, a prodrug compound of this invention should be active only in assays where the prodrug moiety would be cleaved, typically in in vivo assays. Selected assays are described below.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a disease associated with cell death, or various forms of liver disease. Such diseases include those related to rheumatology and autoimmunity, such as rheumatoid arthritis, osteoarthritis, osteoporosis, systemic lupus erythematosus, scleroderma, chronic thyroiditis, Grave's disease, myasthenia gravis, autoimmune neutropenia, autoimmune hemolytic anemia, thrombocytopenia, juvenile rheumatoid arthritis, gout, Behcet's syndrome, Still's syndrome, macrophage activation syndrome, and sarcoidosis; autoinflammatory syndromes, such as cryopyrin-associated Periodic Syndromes (sometimes referred to as autoinflammatory fever syndromes), (including Muckle-Wells syndrome, familial cold urticaria (also known as familial cold autoinflammatory syndrome), chronic infantile neurological cutaneous and articular syndrome (a.k.a. neonatal onset multisystem inflammatory disease)), familial mediterranean fever, TNFR1-Associated Periodic Syndrome (TRAPS), Hyper-IgD periodic fever Syndrome (HIDS), and Blau's syndrome, as well as systemic onset juvenile idiopathic arthritis (also known as Still's disease), and macrophage activation syndrome; dermatology, such as psoriasis, atopic dermatitis, scarring, alopecia, acne vulgaris, and pemphigus, as well as toxic epidermal necrolysis; respiratory, such as asthma, adult respiratory distress syndrome, cystic fibrosis, emphysema, chronic bronchitis, chronic obstructive pulmonary disease, and idiopathic pulmonary fibrosis; internal medicine, such as inflammatory peritonitis, inflammatory bowel disease, Crohn's disease, ulcerative colitis, autoimmune gastritis, *H. pylori*-associated gastric and duodenal ulcer disease, diabetes, pancreatitis, glomerulonephritis, chronic active hepatitis, excess dietary alcohol intake disease, renal disease, polycystic kidney disease, burns, organ apoptosis after burn injury, haemorrhagic shock, organ failure (e.g., hepatic failure, acute renal failure, and acute respiratory failure), and endometriosis; transplants, such as graft vs. host disease (GVHD) and organ transplant rejection; oncology, such as leukemias and related disorders, myelodysplastic syndrome, multiple myeloma-related bone disorder, acute myelogenous leukemia, chronic myelogenous leukemia, metastatic melanoma, Kaposi's sarcoma, and multiple myeloma; cardiovascular, such as chronic heart disease, acute heart disease, myocardial infarction, myocardial ischemia, congestive heart failure, atherosclerosis, coronary artery bypass graft (CABG), and acute coronary syndrome; the central and peripheral nervous systems, such as Alzheimer's disease, Parkinson's disease, Huntington's disease, Kennedy's disease, prion disease, cerebral ischemia, epilepsy, spinal muscular atrophy, amyotrophic lateral sclerosis, multiple sclerosis, HIV-related encephalitis, traumatic brain injury, spinal cord injury, neurological damage due to stroke, diabetic neuropathy, and acute and chronic pain, as well as seizures, seizure disorders, and convulsions; ophthalomology, such as uveitis, retinal disorders, diabetic retinopathy, glaucoma, and keratitis, as well as eye infections, injuries, allergies, chemical irritations, burns, dry eye, Sjogren's syndrome, and aging of the eye (see, e.g., WO 2005/053665, which is incorporated by reference); infectious diseases, such as viral mediated disease, sepsis, septic shock, Shigellosis, hepatitis-B, hepatitis-C, hepatitis-G, yellow fever, dengue fever, Japanese encephalitis, HIV infection, tuberculosis, meningitis, Pseudomonas infection, and Acinetobacter infection, as well as other bacterial, viral, parasitic, or fungal infections, particularly eye infections; and other diseases, such as aging. The compounds and compositions are also useful in treating complications associated with coronary artery bypass grafts. The amount of compound present in the above-described compositions should be sufficient to cause a detectable decrease in the severity of the disease or in caspase activity and/or cell apoptosis, as measured by any of the assays known in the art.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention. Accordingly, a combined preparation for simultaneous, separate, or sequential use is provided by this invention.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of a disease involving caspase activity and/or apoptosis.

Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10 to 100%, and more preferably between about 10 to 80% of the dosage normally administered in a monotherapy regimen.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

In order that this invention be more fully understood, the following preparative and testing examples are set forth. These examples are for the purpose of illustration only and are not to be construed as limiting the scope of the invention in any way. $^1$H-NMR spectra were recorded at 400 MHz using a Bruker DPX 400 instrument. Mass spec. samples were analyzed on a MicroMass Quattro Micro mass spectrometer operated in single MS mode with electrospray ionization.

Example II.1

3(R,S)-[2(S)-(3-Benzoylamino-2-oxo-2H-pyridin-1-yl)-3-phenyl-propionylamino]-5-fluoro-4-oxo-pentanoic acid

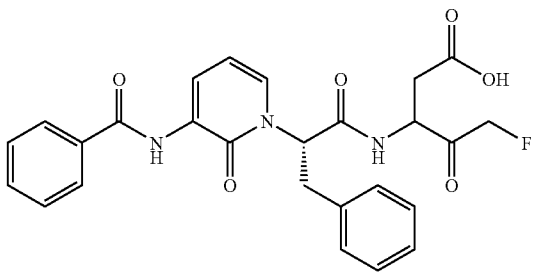 [SMILES: O=C(O)CC(NC(=O)[C@H](Cc1ccccc1)n1cccc(NC(=O)c2ccccc2)c1=O)C(=O)CF]

Method A (S)-2-(3-Benzyloxycarbonylamino-2-oxo-2H-pyridin-1-yl)-3-phenyl-propionic acid tert-butyl ester

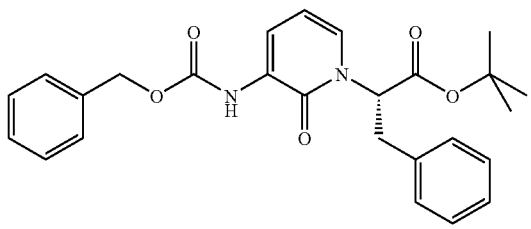 [SMILES: CC(C)(C)OC(=O)[C@H](Cc1ccccc1)n1cccc(NC(=O)OCc2ccccc2)c1=O]

To a cooled (0° C.) solution of (R)-2-Hydroxy-3-phenyl-propionic acid tert-butyl ester (2.50 g, 15.6 mmol) in dichloromethane (50 mL), was slowly added 2,6-lutidine (3.3 g, 30.8 mmol) and then trifluoromethanesulfonic anhydride (8.25 g, 29.2 mmol). The resulting mixture was stirred at 0° C. for 1 hour, then partitioned between tert-butylmethyl ether (200 mL) and an aqueous solution of 1M HCl (60 mL). The organic layer was washed with brine (60 mL), dried (sodium sulfate), filtered and concentrated to afford the triflate as a light brown oil.

To a solution of (2-oxo-1,2-dihydro-pyridin-3-yl)-carbamic acid benzyl ester (P. Warner et al., J. Med. Chem., 37, 19, 1994, 3090-3099)(4.34 g, 17.8 mmol) in dry THF (100 mL) was added sodium hydride (60% dispersion, 711 mg, 17.8 mmol) and the solution was stirred at room temperature for 45 minutes. The reaction mixture was then slowly transferred with a canula onto a solution of the triflate prepared above in THF (30 mL). The reaction mixture was stirred at room temperature for 90 minutes and quenched with aqueous ammonium chloride (20 mL). Most of the solvent was evaporated and the residue was partitioned between EtOAc and saturated aqueous $NH_4Cl$. The organic layer was washed with brine (30 mL), dried ($MgSO_4$), filtered and evaporated. The residue was purified by flash chromatography (10% ethyl acetate/hexane) to afford the title compound as a colourless oil (5.1 g, 76%); $^1$H NMR (400 MHz, $CDCl_3$) δ 1.48 (9H, s), 3.35 (1H, dd), 3.65 (1H, dd), 5.23 (2H, s), 5.53 (1H, m), 6.18 (1H, t), 6.85 (1H, d), 7.12 (2H, m), 7.20-7.48 (8H, m), 7.82 (1H, s), 7.98 (1H, m).

Method B (S)-2-(3-Amino-2-oxo-2H-pyridin-1-yl)-3-phenyl-propionic acid tert-butyl ester

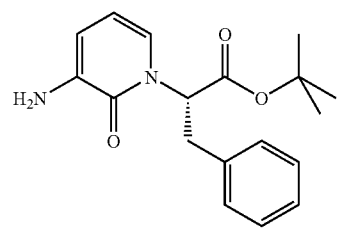 [SMILES: CC(C)(C)OC(=O)[C@H](Cc1ccccc1)n1cccc(N)c1=O]

To a solution of (S)-2-(3-benzyloxycarbonylamino-2-oxo-2H-pyridin-1-yl)-3-phenyl-propionic acid tert-butyl ester (4 g, 8.92 mmol) in a mixture of MeOH (40 mL) and EtOAc (10 mL) was added 10% Pd/C (500 mg). The mixture was degassed and stirred at room temperature for 4 hours under an atmosphere of hydrogen (balloon pressure). The reaction mixture was filtered through a short pad of celite which was then flushed with MeOH. The combined filtrates were evaporated under reduced pressure to afford the title compound as a white solid (2.6 g, 92%); $^1$H NMR (400 MHz, CDCl$_3$) δ 1.48 (9H, s), 3.32 (1H, dd), 3.52 (1H, dd), 3.95 (2H, br s), 5.55 (1H, dd), 6.00 (1H, t), 6.55 (1H, d), 6.72 (1H, d), 7.18-7.35 (5H, m).

Method C (S)-2-(3-Benzoylamino-2-oxo-2H-pyridin-1-yl)-3-phenyl-propionic acid tert-butyl ester

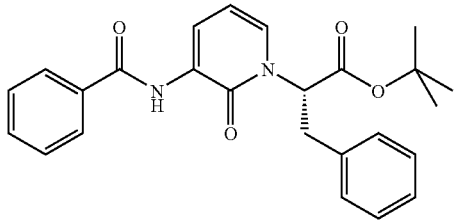 [SMILES: CC(C)(C)OC(=O)[C@H](Cc1ccccc1)n1cccc(NC(=O)c2ccccc2)c1=O]

To a cooled (0° C.) solution of (S)-2-(3-amino-2-oxo-2H-pyridin-1-yl)-3-phenyl-propionic acid tert-butyl ester (2.6 g, 8.26 mmol) in dichloromethane (50 mL) was added triethylamine (918 mg, 9.09 mmol) and DMAP (20 mg) followed by dropwise addition of benzoyl chloride (1.27 g, 9.1 mmol). The reaction mixture was stirred at room temperature for 12 hours and then partitioned between EtOAc and sat. aqueous NH$_4$Cl. The organic layer was washed with water (30 ml), brine (30 mL), dried (MgSO$_4$), filtered and evaporated. The residue was purified by flash chromatography (10-25% ethyl acetate/petrol ether) to afford the title compound as a colourless oil (2.07 g, 60%); $^1$H NMR (400 MHz, CDCl$_3$) δ 1.48 (9H, s), 3.35 (1H, dd), 3.55 (1H, dd), 5.5 (1H, m), 6.26 (1H, t), 6.90 (1H, d), 7.15 (2H, m), 7.28 (3H, m), 7.52 (3H, m), 7.95 (2H, m), 8.52 (1H, d), 9.22 (1H, br s).

Method D (S)-2-(3-Benzoylamino-2-oxo-2H-pyridin-1-yl)-3-phenyl-propionic acid

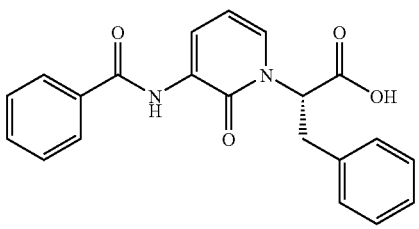 [SMILES: O=C(Nc1cccn([C@@H](Cc2ccccc2)C(=O)O)c1=O)c1ccccc1]

A solution of (S)-2-(3-benzoylamino-2-oxo-2H-pyridin-1-yl)-3-phenyl-propionic acid tert-butyl ester (2.07 g, 4.95 mmol) in dichloromethane (25 mL) was cooled to 0° C. Trifluoroacetic acid (25 ml) was added and the resulting mixture allowed to warm to room temperature and stir for 5 hours. The mixture was then concentrated under reduced pressure and the residue re-dissolved in dichloromethane. This process was repeated several times in order to remove excess trifluoroacetic acid. The resulting solid was slurried in diethyl ether, filtered and washed with more diethyl ether. The solid was then dried to constant weight under vacuum. This gave the title product as a white solid (1.61 g, 90%); $^1$H NMR (400 MHz, CDCl$_3$) δ 3.48 (1H, dd), 3.65 (1H, dd), 5.32 (1H, m), 6.35 (1H, t), 6.80 (1H, m), 7.08 (2H, d), 7.27-7.35 (3H, m), 7.56-7.65 (3H, m), 7.92 (2H, d), 8.65 (1H, d), 9.18 (1H, br s).

Method E

3(R,S)-[2(S)-(3-Benzoylamino-2-oxo-2H-pyridin-1-yl)-3-phenyl-propionylamino]-5-fluoro-4(R,S)-hydroxy-pentanoic acid tert-butyl ester

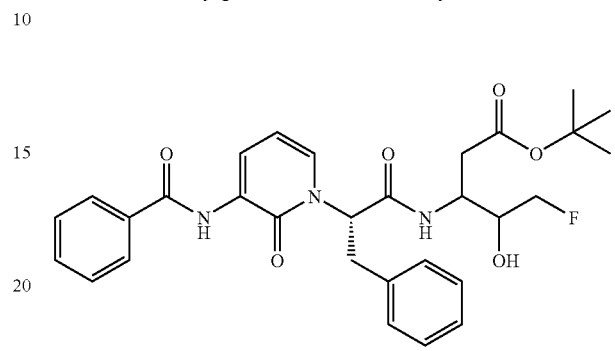

A stirred mixture of (S)-2-(3-benzoylamino-2-oxo-2H-pyridin-1-yl)-3-phenyl-propionic acid (2.20 g, 6.07 mmol), 3(R,S)-Amino-5-fluoro-4(R,S)-hydroxy-pentanoic acid tert-butyl ester (1.39 g, 6.68 mmol), HOBt (902 mg, 6.68 mmol), DMAP (853 mg, 6.98 mmol) and THF (20 mL) was cooled to 0° C. then EDC (1.28 mg, 6.68 mmol) was added. The mixture was allowed to warm to room temperature during 16 h then concentrated under reduced pressure. The residue was purified by flash chromatography (30-70 to 55-45% ethyl acetate/hexane) to afford the title compound as a white foam (1.23 g, 32%); $^1$H NMR (400 MHz, CDCl$_3$) δ 0.88-0.93 (3H, m), 1.35-1.42 (9H, 2s), 2.50-2.65 (2H, m), 3.20-3.35 (2H, m), 3.60 (1H, m), 3.98 (1H, m), 4.10-4.32 (3H, m), 5.62-5.70 (1H, m), 6.44 (1H, m), 6.80-6.98 (1H, m), 7.21-7.41 (5H, m), 7.55-7.62 (3H, m), 7.95 (2H, m), 8.58 (1H, t), 9.18 (1H, br s).

Method F

3(R,S)-[2(S)-(3-Benzoylamino-2-oxo-2H-pyridin-1-yl)-3-phenyl-propionylamino]-5-fluoro-4-oxo-pentanoic acid tert-butyl ester

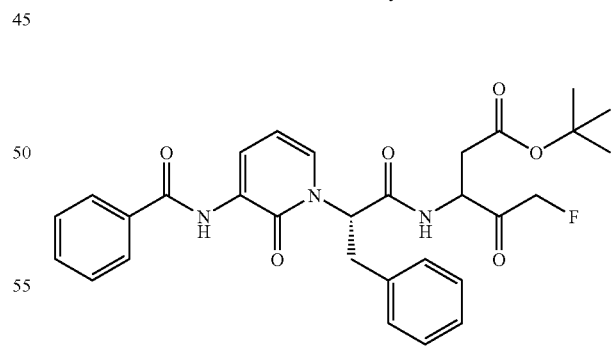

A stirred solution of 3(R,S)-[2(S)-(3-benzoylamino-2-oxo-2H-pyridin-1-yl)-3-phenyl-propionylamino]-5-fluoro-4 (R,S)-hydroxy-pentanoic acid tert-butyl ester (1.23 g, 2.23 mmol) in anhydrous DCM (25 mL) was treated with 1,1,1-triacetoxy-1,1-dihydro-1,2-benziodoxol-3(1H)-one (Dess-Martin periodinane) (1.13 g, 2.67 mmol) at 0° C. The resulting mixture was kept at 0° C. for 2 hours, diluted with ethyl acetate, then poured into a 1:1 mixture of saturated aqueous sodium hydrogen carbonate and saturated aqueous sodium thiosulfate. The organic layer was removed and the aqueous layer re-extracted with ethyl acetate. The combined organic extracts were dried (Magnesium sulfate) and concentrated. The residue was purified by flash chromatography (40-60% ethyl acetate/petrol ether) to afford the title compound as a red gum (776 mg, 64%); $^1$H NMR (400 MHz, CDCl$_3$) δ 1.32-1.40 (3H, s), 2.60 (1H, m), 2.92 (1H, m), 3.27 (1H, m), 3.61 (1H, m), 4.78-4.88 (1H, m), 4.97-5.05 (2H, m), 5.77 (1H, m), 6.43 (1H, m), 7.22-7.38 (7H, m), 7.54-7.65 (3H, m), 7.95 (2H, m), 8.62 (1H, m), 9.22 (1H, m).

Method G

3(R,S)-[2(S)-(3-Benzoylamino-2-oxo-2H-pyridin-1-yl)-3-phenyl-propionylamino]-5-fluoro-4-oxo-pentanoic acid

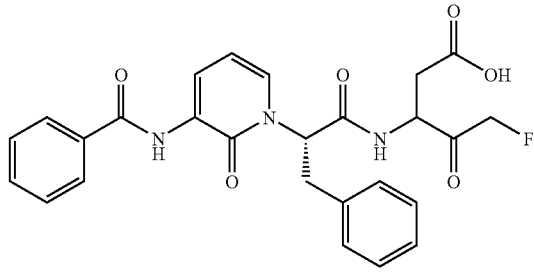 [SMILES: O=C(O)CC(NC(=O)[C@H](Cc1ccccc1)n1cccc(NC(=O)c2ccccc2)c1=O)C(=O)CF]

A solution of 3(R,S)-[2(S)-(3-benzoylamino-2-oxo-2H-pyridin-1-yl)-3-phenyl-propionylamino]-5-fluoro-4-oxo-pentanoic acid tert-butyl ester (776 mg, 1.41 mmol) in dichloromethane (6 mL) was cooled to 0° C. Trifluoroacetic acid (2 ml) was added and the resulting mixture allowed to warm to room temperature and stir for 3 hours. The mixture was then concentrated under reduced pressure and the residue redissolved in dichloromethane. This process was repeated several times in order to remove excess trifluoroacetic acid. The solid was then dried to constant weight under vacuum. This gave the title product as a pink solid (627 mg, 90%); $^1$H NMR (400 MHz, d6-DMSO) δ 2.59-2.95 (2H, m), 3.34-3.47 (2H, m), 4.30-4.81 (2H, m), 5.15-5.33 (2H, m), 5.87-6.09 (1H, m), 6.38 (1H, t), 7.15-7.32 (5H, m), 7.60-7.78 (4H, m), 7.92 (2H, d), 8.17-8.21 (1H, m), 9.01-9.11 (1H, m), 9.28 (1H, m), 12.51 (1H, br s); $^{19}$F NMR (376 MHz, d6-DMSO, proton-decoupled) δ−226.8, 232.6; M+H 494.4, M−H 492.4.

Example II.2

3(R,S)-[2(S)-(3-Benzoylamino-2-oxo-2H-pyridin-1-yl)-4-phenyl-butyrylamino]-5-fluoro-4-oxo-pentanoic acid

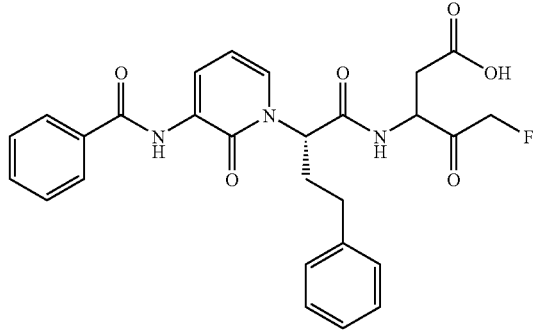 [SMILES: O=C(O)CC(NC(=O)[C@H](CCc1ccccc1)n1cccc(NC(=O)c2ccccc2)c1=O)C(=O)CF]

Prepared according to methods A and D-G using N-(2-Oxo-1,2-dihydro-pyridin-3-yl)-benzamide and (R)-2-hydroxy-4-phenyl-butyric acid tert-butyl ester (prepared using a method similar to that reported in Lei et al., J. Carbohydrate Chemistry, 15, 4, 1996, 485-500) in method A; white solid; IR (solid) 1643, 1578, 1521, 1490, 1213, 753 cm$^{-1}$; $^1$H NMR (400 Mhz, d6-DMSO) δ 2.3-2.9 (6H, m), 3.5-3.7 (2H, m), 4.3-4.7 (3H, m), 5.1-5.35 (1.5H, m), 5.6-5.8 (1H, m), 6.4-6.45 (1H, m), 7.2-7.35 (5H, m), 7.6-7.8 (4H, m), 7.9-8.0 (2H, m), 8.3-8.35 (1H, m), 8.9-9.0 (1H, m), 9.35-9.4 (1H, m); M+H 508.4, M−H 506.4.

Example II.3

3(R,S)-[2(S)-(3-Benzoylamino-5-methyl-2-oxo-2H-pyridin-1-yl)-3-phenyl-propionylamino]-5-fluoro-4-oxo-pentanoic acid

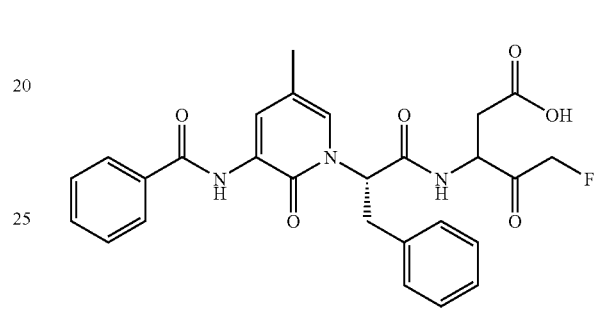

Prepared according to methods A and D-G using N-(5-methyl-2-oxo-1,2-dihydro-pyridin-3-yl)-benzamide and (R)-2-Hydroxy-3-phenyl-propionic acid tert-butyl ester in step A; white solid; IR (solid) 1650, 1516, 1224, 692 cm$^{-1}$; $^1$H NMR (400 MHz, d6-DMSO) δ 0.83-0.86 (3H, m), 2.30-2.67 (4H, m), 4.32-4.95 (2H, m), 5.12-5.24 (1H, m), 5.83-6.04 (1H, m), 7.15-7.61 (9H, m), 7.86-7.88 (2H, m), 8.11-8.12 (1H, m, 8.70-9.02 (1H, m), 9.21 (1H, d), 12.41 (1H, br s); M+H 508.4, M−H 506.4.

Example II.4

3(R,S)-{2(S)-[3-(2,6-Dimethyl-benzoylamino)-2-oxo-2H-pyridin-1-yl]-3-phenyl-propionylamino}-5-fluoro-4-oxo-pentanoic acid

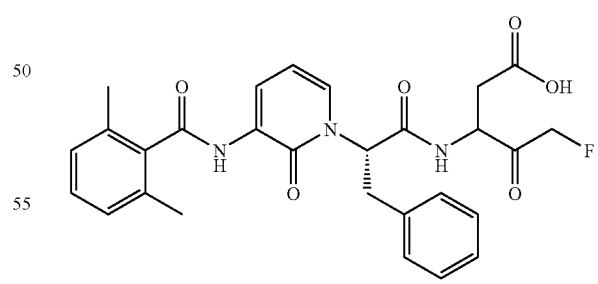

Prepared according to methods A-G using 2,6 dimethyl-benzoyl chloride in method C; off-white solid; $^1$H NMR (400 MHz, d6-DMSO) δ2.50 (6H, s), 2.51-2.98 (2H, m), 3.15-3.45 (2H, m), 4.15-3.30 (3H, m), 5.61-6.00 (1H, m), 6.25 (1H, m), 7.00-7.25 (8H, m), 7.45-7.70 (1H, m), 8.12 (1H, m), 8.65-9.10 (2H, m); $^{19}$F (376 MHz, d6-DMSO, proton-decoupled) δ −226.8, −226.8, −227.5, −230.8, −231.8, −232.7, −232.8, −232.8, −232.9, −233.4; M+H 522.5, M−H 520.5.

Example II.5

3(R,S)-{2(S)-[3-(2,6-Dichloro-benzoylamino)-2-oxo-2H-pyridin-1-yl]-3-phenyl-propionylamino}-5-fluoro-4-oxo-pentanoic acid

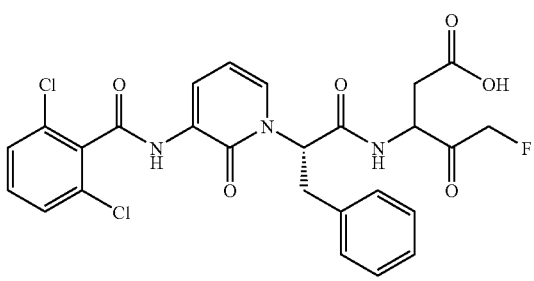 [SMILES: O=C(O)CC(NC(=O)[C@H](Cc1ccccc1)n1cccc(NC(=O)c2c(Cl)cccc2Cl)c1=O)C(=O)CF]

Prepared according to methods A-G using 2,6 dichloro-benzoyl chloride in method C; $^1$H NMR (400 MHz, d6-DMSO) δ 2.35-2.99 (2H, m), 3.05-3.50 (2H, m), 4.15-5.35 (3H, m), 5.66-6.05 (1H, m), 6.29 (1H, m), 7.10-7.30 (5H, m), 7.37-7.52 (3H, m), 7.51-7.70 (1H, m), 8.25 (1H, m), 8.70-9.11 (1H, m), 10.00-10.15 (1H, m); $^{19}$F (376 MHz, d6-DMSO, proton-decoupled) δ −226.7, −226.8, −230.7, −231.4, −232.6, −232.7, −232.9; M+H 562.28, M−H 560.28.

Example II.6

3(R,S)-{2(S)-[3-(3,3-Diethyl-ureido)-2-oxo-2H-pyridin-1-yl]-3-phenyl-propionylamino}-5-fluoro-4-oxo-pentanoic acid

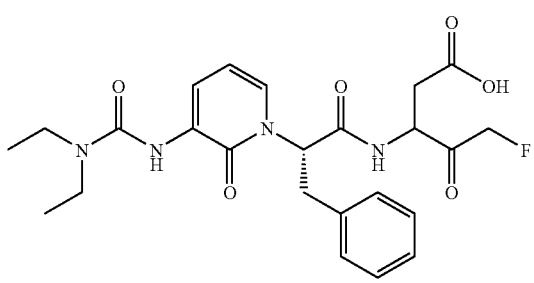 [SMILES: CCN(CC)C(=O)Nc1cccn([C@@H](Cc2ccccc2)C(=O)NC(CC(=O)O)C(=O)CF)c1=O]

Method H (S)-2-[3-(3,3-Diethyl-ureido)-2-oxo-2H-pyridin-1-yl]-3-phenyl-propionic acid tert-butyl ester

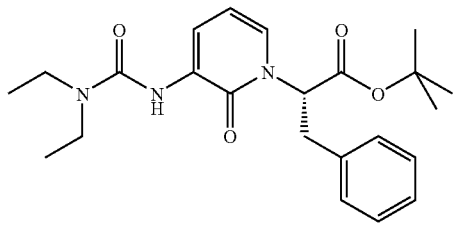 [SMILES: CCN(CC)C(=O)Nc1cccn([C@@H](Cc2ccccc2)C(=O)OC(C)(C)C)c1=O]

To a cooled (0° C.) solution of (S)-2-(3-Amino-2-oxo-2H-pyridin-1-yl)-3-phenyl-propionic acid tert-butyl ester (500 mg, 1.59 mmol) in dichloroethane (3 mL) was added triethylamine (0.254 mL, 1.82 mmol). This solution was added dropwise to a solution of diphosgene (0.11 mL, 0.91 mmol) in dichloroethane (7 mL) at 0° C. over 10 minutes. The reaction mixture was stirred at room temperature for 90 minutes and then partitioned between EtOAc and aqueous 1M HCl. The organic layer was washed with brine, dried (MgSO$_4$), filtered and evaporated to afford the isocyanate as a brown oil.

To a cooled (0° C.) solution of the isocyanate prepared above (541 mg, 1.59 mmol) in dichloroethane (8 mL) was added triethylamine (0.24 mL, 1.75 mmol) followed by diethylamine (0.16 mL, 1.59 mmol). The reaction mixture was stirred at room temperature for 3 hours and then partitioned between EtOAc and aqueous 1M HCl. The organic layer was washed with brine, dried (MgSO$_4$), filtered and evaporated to afford a brown oily residue which was purified by flash column chromatography (25-75% ethyl acetate/hexane) to afford the diethylurea as a light pink oil. $^1$H NMR (400 MHz, CDCl$_3$) δ 1.48 (9H, s), 3.35 (1H, dd), 3.55 (1H, dd), 5.5 (1H, m), 6.26 (1H, t), 6.90 (1H, d), 7.15 (2H, m), 7.28 (3H, m), 7.52 (3H, m), 7.95 (2H, m), 8.52 (1H, d), 9.22 (1H, br s).

This intermediate was involved in the sequence described in methods D-G to afford example II.6 as a pale pink solid; IR (solid) 1794, 1737, 1664, 1640, 1588, 1515, 1458, 1414, 1382, 1353, 1220, 1066 cm$^{-1}$; $^1$H NMR (400 MHz, d6-DMSO) δ 1.08-1.12 (6H, m), 2.50-2.90 (2H, m), 3.20-3.55 (6H, m), 4.30-5.30 (3H, m), 5.85 (1H, m), 6.19 (1H, m), 7.15-7.37 (6H, m), 7.64 (1H, m), 7.86 (1H, m), 9.00 (1H, m); $^{19}$F (376 MHz, d6-DMSO, proton-decoupled) δ −226.8, −226.8, −230.8, −231.6, −232.9, −233.0; M+H 489.4 M−H 487.4.

Example II.7

5-Fluoro-4-oxo-3(R,S)-[2(S)-(2-oxo-3-phenylacetylamino-2H-pyridin-1-yl)-3-phenyl-propionylamino-pentanoic acid

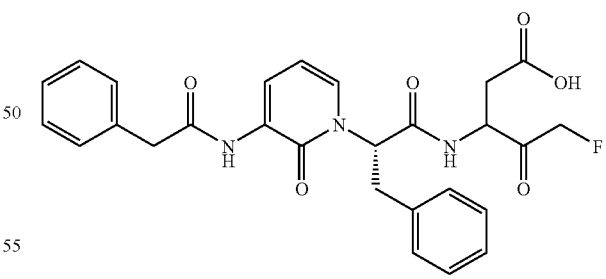

Prepared according to methods A-G using phenyl acetyl chloride in method C; Pale pink solid; IR (solid) 1789, 1742, 1685, 1643, 1587, 1516, 1451 cm$^{-1}$; $^1$H NMR (400 MHz, d6-DMSO) δ 2.50-2.90 (2H, m), 3.27-3.41 (2H, m), 3.76 (2H, s), 4.30-5.30 (3H, m), 5.90 (1H, m), 6.17 (1H, m), 7.15-7.31 (10H, m), 7.50 (1H, m), 8.00 (1H, m), 8.85 (1H, m), 9.25 (1H, m); $^{19}$F (376 MHz, d6-DMSO, proton-decoupled) δ −222.0, −222.1, −226.0, −226.5, −227.9, −228.0; M+H 508.5, M−H 506.5.

Example II.8

3(S)-{2(S)-[3-(2,6-Dichloro-benzoylamino)-2-oxo-2H-pyridin-1-yl]-3-phenyl-propionylamino}-4-oxo-5-(2,3,5,6-tetrafluoro-phenoxy)-pentanoic acid

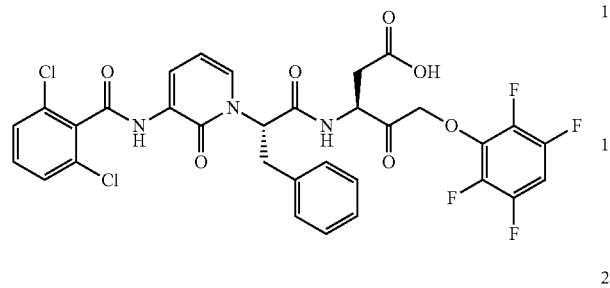

Prepared according to methods A-G using 2,6 dichlorobenzoyl chloride in method C and 3(S)-Amino-4(R,S)-hydroxy-5-(2,3,5,6-tetrafluoro-phenoxy)-pentanoic acid tert-butyl ester in step E; Pink Solid; IR (solid) 1675, 1634, 1511, 1429 cm$^{-1}$; $^1$H NMR (400 MHz, d6-DMSO) δ 2.61-2.80 (2H, m), 3.29-3.52 (2H, m), 4.67-4.73 (1H, m), 5.22 (2H, dd), 5.87-5.93 (1H, m), 6.26-6.31 (1H, m), 7.12-7.28 (5H, m), 7.41-7.72 (5H, m), 8.26 (1H, d), 9.12 (1H, d), 10.05 (1H, s); $^{19}$F (376 MHz, d6-DMSO, proton-decoupled) δ −140.5, −140.6, −140.6, −140.6, −141.0, −141.0, −141.0, −141.1, −156.9, −156.9, −156.9, −156.9, −157.0; M+H 708.1 M−H 706.0.

Example II.9

5-Fluoro-4-oxo-3(R,S)-{2(S)-[2-oxo-3-(3-phenyl-ureido)-2H-pyridin-1-yl]-3-phenyl-propionylamino}-pentanoic acid

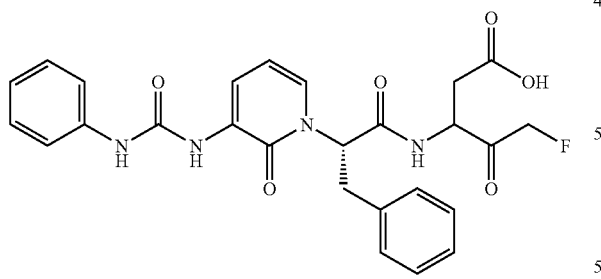

Prepared according to methods A-G using phenyl isocyanate in method C; Off white solid; IR (solid) 1780, 1737, 1671, 1638, 1601, 1544, 1498 cm$^{-1}$; $^1$H NMR (400 MHz, d6-DMSO) δ2.50-2.90 (2H, m), 3.20-3.55 (2H, m), 4.30-5.30 (3H, m), 5.90 (1H, m), 6.20 (1H, m), 6.85 (1H, m), 7.10-7.45 (11H, m), 8.00 (1H, m), 8.50 (1H, m), 9.00 (1H, m), 9.50 (1H, m), 12.50 (1H, br s); $^{19}$F (376 MHz, d6-DMSO, proton-decoupled) δ−226.8, −226.8, −227.5, −230.9, −231.3, −232.7, −232.8, −233.4; M+H 509.5 M−H 507.45.

Example II.10

3(R,S)-[2(S)-(3-Benzoylamino-2-oxo-5-trifluoromethyl-2H-pyridin-1-yl)-3-phenyl-propionylamino]-5-fluoro-4-oxo-pentanoic acid

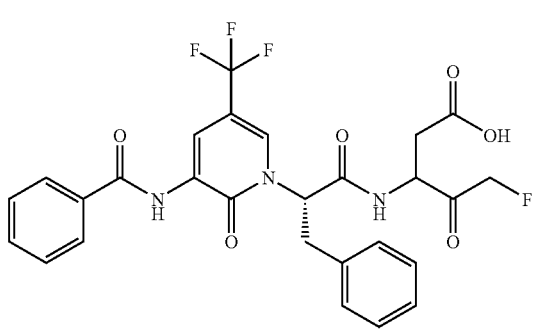 [SMILES: O=C(O)CC(NC(=O)[C@H](Cc1ccccc1)n1cc(C(F)(F)F)cc(NC(=O)c2ccccc2)c1=O)C(=O)CF]

Prepared from N-(2-oxo-5-trifluoromethyl-1,2-dihydro-pyridin-3-yl)-carbamic acid benzyl ester according to methods A-G; IR solid 1655, 1521, 1450, 1322, 1173, 1127 cm$^{-1}$; $^1$H NMR (400 MHz, d6-DMSO) δ 2.60-2.91 (2H, m), 3.45-3.64 (2H, m), 4.65 (1H, m), 5.18-5.37 (2H, m), 5.81-5.97 (1H, m), 7.16-7.25 (5H, m), 7.52-7.63 (3H, m), 7.89-7.91 (2H, m), 8.02-8.14 (1H, m), 8.35 (1H, s), 9.10-9.19 (1H, m), 9.41 (1H, br s), 12.69 (1H, br s); $^{19}$F (376 MHz, d6-DMSO, proton-decoupled) δ−61.3. −61.3, −226.7, −226.9, −232.6, −232.7; M+H 562.4, M−H 560.4.

Example II.11

5-Fluoro-3(R,S)-[2(S)-(3-isobutyrylamino-2-oxo-2H-pyridin-1-yl)-3-phenyl-propionylamino]-4-oxo-pentanoic acid

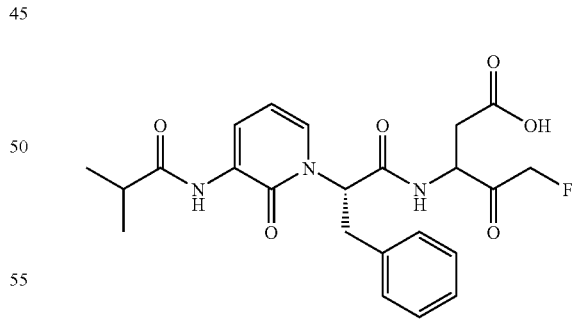

Prepared according to methods A-G using isobutyryl chloride in method C; off-white solid; $^1$H NMR (400 MHz, d6-DMSO) δ 1.05 (6H, m), 2.50-2.99 (3H, m), 3.11-3.50 (2H, m), 4.20-5.35 (3H, m), 5.70-6.10 (1H, m), 6.21 (1H, m), 7.07-7.28 (5H, m), 7.40-7.60 (1H, m), 7.85-8.15 (1H, m), 8.65-9.10 (2H, m); $^{19}$F (376 MHz, d6-DMSO, proton-decoupled) δ−226.7, −226.8, −230.7, −231.3, −232.7, −232.7; M+H 460.2, M−H 458.2.

Example II.12

3(R,S)-[2(S)-(3-Benzoylamino-2-oxo-2H-pyridin-1-yl)-3-thiophen-3-yl-propionylamino]-5-fluoro-4-oxo-pentanoic acid

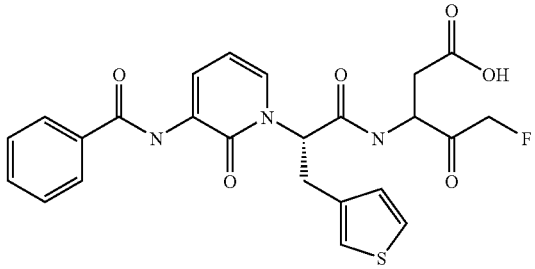 [SMILES: O=C(O)CC(NC(=O)[C@H](Cc1ccsc1)n1cccc(NC(=O)c2ccccc2)c1=O)C(=O)CF]

Prepared according to methods A and D-G using N-(2-Oxo-1,2-dihydro-pyridin-3-yl)-benzamide and 2-Hydroxy-3-thiophen-3-yl-propionic acid tert-butyl ester (prepared using a method similar to that reported in Lei et al., J. Carbohydrate Chemistry, 15, 4, 1996, 485-500) in method A; IR (solid) 1675, 1644, 1578, 1521, 705 cm$^{-1}$; $^1$H NMR (400 Mhz, d6-DMSO) δ 2.6-2.9 (2H, m), 3.5-3.7 (2H, m), 4.3-4.7 (3H, m), 5.1-5.35 (2H, m), 5.7-5.9 (1H, m), 6.3-6.4 (1H, m), 6.8-6.9 (2H, m), 7.15-7.2 (1H, m), 7.3-7.35 (1H, m), 7.4-7.6 (4H, m), 7.9-7.9 (2H, m), 8.2-8.25 (1H, m), 9.0-9.1 (1H, m), 9.25-9.3 (1H, m); M+H 500.4, M−H 498.4.

Example II.13

5-Fluoro-4-oxo-3(R,S)-[2(S)-(2-oxo-3-propionylamino-2H-pyridin-1-yl)-3-phenyl-propionylamino]-pentanoic acid

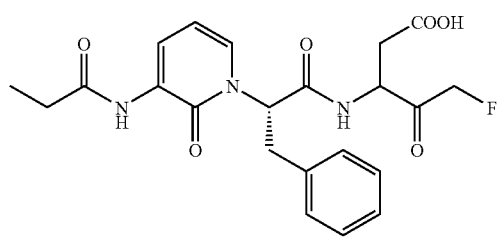 [SMILES: CCC(=O)Nc1cccn([C@@H](Cc2ccccc2)C(=O)NC(CC(=O)O)C(=O)CF)c1=O]

Prepared according to methods A-G using propionyl chloride in method C; beige solid; $^1$H NMR (400 Mhz, d6-DMSO) δ0.99-1.02 (3H, m), 2.36-2.42 (2H, m), 2.53-2.94 (2H, m), 3.21-3.45 (3H, m), 4.33-5.29 (3H, m), 5.80-6.02 (1H, m), 6.16-6.21 (1H, m), 7.11-7.23 (5H, m), 7.43-7.53 (1H, m), 8.08-8.13 (1H, m), 8.68-9.05 (2H, m), 12.50 (1H, br s); M+H 446.4, M−H 444.4.

Example II.14

3(R,S)-[2(S)-(3-Benzoylamino-2-oxo-2H-pyridin-1-yl)-3-thiophen-2-yl-propionylamino]-5-fluoro-4-oxo-pentanoic acid

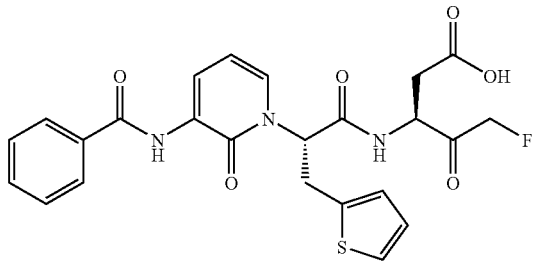 [SMILES: O=C(O)C[C@H](NC(=O)[C@H](Cc1cccs1)n1cccc(NC(=O)c2ccccc2)c1=O)C(=O)CF]

Prepared according to methods A and D-G using N-(2-Oxo-1,2-dihydro-pyridin-3-yl)-benzamide and 2-hydroxy-3-thiophen-2-yl-propionic acid tert-butyl ester (prepared using a method similar to that reported in Lei et al., J. Carbohydrate Chemistry, 15, 4, 1996, 485-500) in method A; IR (solid) 1644, 1521, 705 cm$^{1}$; $^1$H NMR (400 MHz, d6-DMSO) δ 2.6-2.9 (2H, m), 3.5-3.7 (2H, m), 4.3-4.7 (3H, m), 5.1-5.35 (1.5H, m), 5.7-5.9 (1H, m), 6.3-6.4 (1H, m), 6.8-6.9 (2H, m), 7.3-7.35 (1H, m), 7.4-7.7 (4H, m), 7.9-8.0 (3H, m), 8.2-8.25 (1H, m), 9.0-9.1 (1H, m), 9.25-9.3 (1H, m); M+H 500.4, M−H 498.4

Example II.15

3(R,S)-[2(S)-(3-Benzoylamino-2-oxo-2H-pyridin-1-yl)-3-(1H-indol-3-yl)-propionylamino]-5-fluoro-4-oxo-pentanoic acid

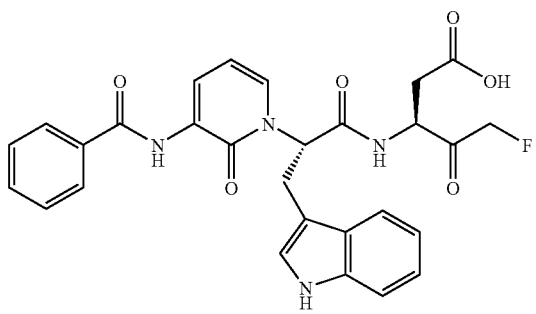 [SMILES: O=C(O)C[C@H](NC(=O)[C@H](Cc1c[nH]c2ccccc12)n1cccc(NC(=O)c2ccccc2)c1=O)C(=O)CF]

Method I (S)-3-[2-tert-Butoxycarbonyl-2-(3-methoxycarbonyl-2-oxo-2H-pyridin-1-yl)-ethyl]-indole-1-carboxylic acid tert-butyl ester

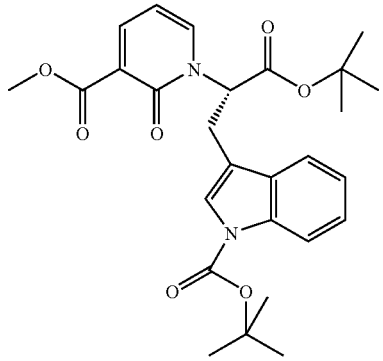 [SMILES: COC(=O)c1cccn([C@@H](Cc2cn(C(=O)OC(C)(C)C)c3ccccc23)C(=O)OC(C)(C)C)c1=O]

To a solution of (S)-3-(2-Amino-2-tert-butoxycarbonyl-ethyl)-indole-1-carboxylic acid tert-butyl ester (2.5 g, 7 mmol) in methanol (15 ml) was added 2-(3-methoxy-allylidene)-malonic acid dimethyl ester (1.5 g, 7 mmol) and stirred overnight at room temperature. Sodium methoxide (78 mg, 1.4 mmol) was added and stirred for three hours at room temperature. The reaction mixture was diluted with water (50 ml) and extracted with ethylacetate (60 ml). The organic layer was washed with brine, dried (MgSO$_4$), filtered and evaporated to afford the crude product, which was perified by flash chromatography (30-70% ethylacetate/petroleum ether) to afford the title compound as a white solid (2.3 g, 57%); $^1$H NMR (400 MHz, CDCl$_3$) δ 1.43 (9H, s), 1.72 (9H, s), 3.50 (2H, m), 3.91 (3H, m), 5.68 (1H, br s), 6.08 (1H, t), 7.2-7.5 (5H, m), 8.15 (2H, m); M+H 497.5, M−H 495.5.

Method J (S)-3-[2-tert-Butoxycarbonyl-2-(3-carboxy-2-oxo-2H-pyridin-1-yl)-ethyl]-indole-1-carboxylic acid tert-butyl ester

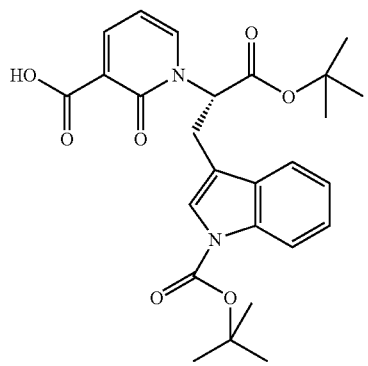 [SMILES: CC(C)(C)OC(=O)[C@H](Cc1cn(C(=O)OC(C)(C)C)c2ccccc12)n1cccc(C(=O)O)c1=O]

To a solution of (S)-3-[2-tert-Butoxycarbonyl-2-(3-methoxycarbonyl-2-oxo-2H-pyridin-1-yl)-ethyl]-indole-1-carboxylic acid tert-butyl ester (2.3 g, 4.7 mmol) in dioxane (60 ml) was added a lithium hydroxide (115 mg, 4.7 mmol) in water (30 ml). The mixture was stirred overnight at room temperature. The mixture was diluted with water, acidified to pH-3 with 1M HCl and extracted with ethylacetate. The organic layer was washed with brine, dried (MgSO$_4$), filtered and evaporated to afford the crude product as a white solid was used in the next stage without further purification (1.9 g, 85%); $^1$H NMR (400 MHz, CDCl$_3$) δ 1.45 (9H, s), 1.74 (9H, s), 3.50 (2H, m), 5.65 (1H, br s), 6.08 (1H, t), 7.2-7.5 (5H, m), 8.15 (2H, m);

Method K

3-[2-(3-Benzyloxycarbonylamino-2-oxo-2H-pyridin-1-yl)-2-tert-butoxycarbonyl-ethyl]-indole-1-carboxylic acid tert-butyl ester

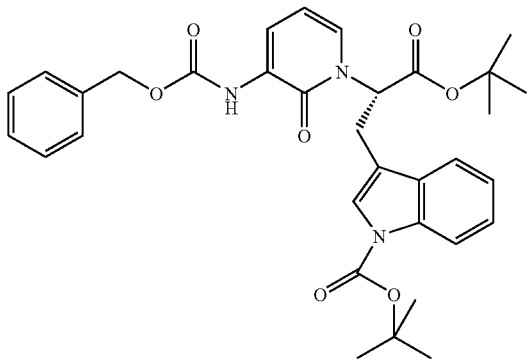 [SMILES: CC(C)(C)OC(=O)[C@H](Cc1cn(C(=O)OC(C)(C)C)c2ccccc12)n1cccc(NC(=O)OCc2ccccc2)c1=O]

To a stirred solution of (S)-3-[2-tert-Butoxycarbonyl-2-(3-carboxy-2-oxo-2H-pyridin-1-yl)-ethyl]-indole-1-carboxylic acid tert-butyl ester (1.8 g, 3.7 mmol) in dioxane was added triethylamine (580 mg, 5.9 mmol), diphenylphosphoryl azide 91.5 g, 5.6 mmol) and benzyl alcohol (680 mg, 6.3 mmol) and the mixture refluxed at 100 C for 18 hours. The mixture was concentrated and partitioned between ethylacetate and saturated bicarbonate. The organic layer was washed with brine, dried (MgSO$_4$), filtered and evaporated to afford the crude product, which was purified by flash chromatography (30-70% ethylacetate/petroleum ether) to afford the title compound as a white solid (1.3 g, 59%); 1H NMR (400 MHz, CDCl$_3$) δ 1.48 (9H, s), 1.73 (9H, s), 3.45 (1H, m), 3.65 (1H, m), 5.2-5.25 (2H, m), 5.60 (1H, m), 6.15 (1H, t), 6.85 (1H, m), 7.25-7.55 (9H, m), 7.95 (1H, m), 8.02-8.18 (2H, m);

The product from method K was involved in the sequence of reactions B-G to afford the title compound as an off white solid; IR (solid) 1669, 1643, 1578, 1522, 1490, 1212 cm$^{-1}$; $^1$H NMR (400 MHz, d6-DMSO) δ 2.5-2.8 (2H, m), 3.4-3.6 (2H, m), 4.35-4.6 (1H, m), 4.65-4.8 (1H, m), 5.15-5.3 (1H, m), 5.85-6.0 (1H, m), 6.3-6.35 (1H, m), 6.9-7.1 (3H, m), 7.25-7.3 (1H, m), 7.5-7.9 (8H, m), 8.2-8.25 (1H, m), 9.1-9.3 (2H, m), 10.8-10.9 (1H, br s); 0.40-7.60 (1H, m), 7.85-8.15 (1H, m), 8.65-9.10 (2H, m); $^{19}$F (376 MHz, d6-DMSO, proton-decoupled) δ−226.3, 226.7, −232.5, −232.6; M+H 533.0, M−H 530.9.

Example II.16

3(R,S)-[2(S)-(3-Ethanesulfonylamino-2-oxo-2H-pyridin-1-yl)-3-phenyl-propionylamino]-5-fluoro-4-oxo-pentanoic acid

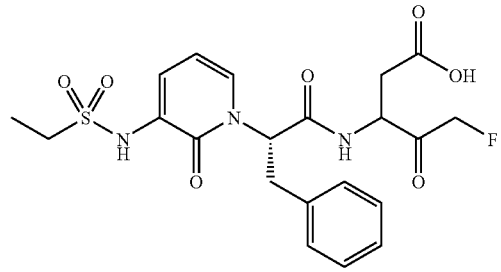 [SMILES: CCS(=O)(=O)Nc1cccn([C@@H](Cc2ccccc2)C(=O)NC(CC(=O)O)C(=O)CF)c1=O]

Prepared according to methods A-G using ethanesulfonyl chloride in method C; Pale blue solid; IR (solid) 1787, 1742, 1685, 1643, 1590, 1551, 1456 cm$^{-1}$; $^1$H NMR (400 MHz, d6-DMSO) δ 1.03-1.14 (3H, m), 2.51-2.94 (4H, m), 3.30-3.41 (2H, m), 4.30-5.30 (3H, m), 5.90 (1H, m), 6.20 (1H, m), 7.14-7.26 (7H, m), 7.58 (1H, m), 8.80 (1H, m); $^{19}$F (376 MHz, d6-DMSO, proton-decoupled) δ−226.8, −230.8, −232.8, −232.9; M+H 482.4 M−H 480.4.

Example II.17

3(R,S)-[4-Benzyloxy-2(S)-(2-oxo-3-propionylamino-2H-pyridin-1-yl)-butyrylamino]-5-fluoro-4-oxo-pentanoic acid

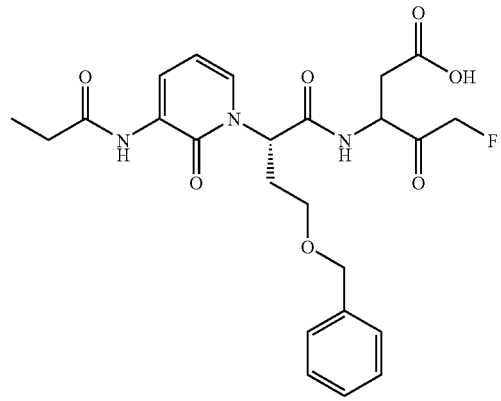 [SMILES: CCC(=O)Nc1cccn([C@@H](CCOCc2ccccc2)C(=O)NC(CC(=O)O)C(=O)CF)c1=O]

Prepared according to the methods A and D-G using (R)-4-benzyloxy-2-hydroxy-butyric acid tert-butyl ester (prepared using a method similar to that reported in Lei et al., J. Carbohydrate Chemistry, 15, 4, 1996, 485-500) in method A; Pale pink solid; IR (solid) 1784, 1740, 1675, 1589, 1515, 1451, 1368 cm$^{-1}$; $^1$H NMR (400 MHz, d6-DMSO) δ 1.23-1.27 (3H, t), 2.20 (1H, m), 2.46-2.48 (2H, m), 2.50 (1H, m), 2.75-3.09 (2H, m), 3.39 (1H, m), 3.55 (1H, m), 4.42-4.50 (3H, m), 4.70-5.01 (2H, m), 5.47-5.87 (1H, m), 6.40 (1H, m), 6.98 (1H, m), 7.02-7.06 (5H, m), 7.68 (1H, m), 8.26 (1H, m), 8.48 (1H, m); $^{19}$F (376 MHz, CDCl$_3$, proton-decoupled) δ −230.2, −230.46, −231.9, −232.4; M+H 490.4, M−H 488.4.

Example II.18

3(R,S)-[3(S)-Benzyloxy-2(S)-(2-oxo-3-propionylamino-2H-pyridin-1-yl)-butyrylamino]-5-fluoro-4-oxo-pentanoic acid

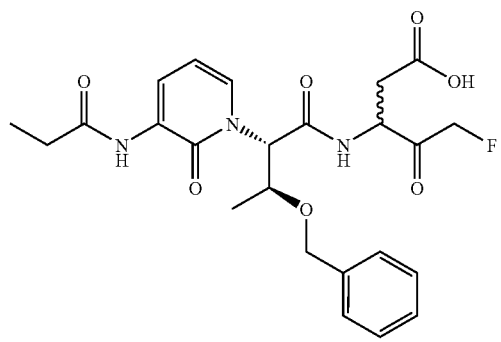 [SMILES: CCC(=O)Nc1cccn([C@H](C(=O)NC(CC(=O)O)C(=O)CF)[C@H](C)OCc2ccccc2)c1=O]

Prepared according to the methods A and D-G using 3(S)-Benzyloxy-2-(R)-hydroxy-butyric acid tert-butyl ester (prepared using a method similar to that reported in Lei et al., J. Carbohydrate Chemistry, 15, 4, 1996, 485-500) in method A; IR (solid) 1738, 1644, 1518, 1371, 1205 cm$^{-1}$; $^1$H NMR (400 MHz, d6-DMSO) δ 1.13-1.25 (3H, m), 1.25-1.35 (3H, m), 2.40-2.5 (2H, m), 2.7-3.2 (2H, m), 4.3-5.2 (6H, m), 6.40-6.5 (1H, m), 7.3-7.55 (5H, m), 7.68 (1H, m), 8.3-8.4 (1H, m), 8.5-8.6 (1H, m); M+H 490.4, M−H 488.4.

Example II.19

5-Fluoro-4-oxo-3(R,S)-[2(R,S)-(2-oxo-3-propionylamino-2H-pyridin-1-yl)-2-phenyl-acetylamino]-pentanoic acid

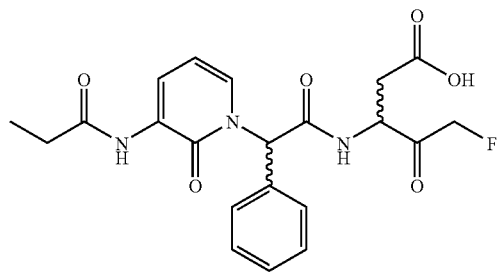 [SMILES: CCC(=O)Nc1cccn(C(C(=O)NC(CC(=O)O)C(=O)CF)c2ccccc2)c1=O]

Prepared according to methods A and D-G using Bromophenyl-acetic acid methyl ester in step A; IR (Solid) 1671, 1643, 1581, 1520 cm$^{-1}$; $^1$H NMR (400 Mhz, d6-DMSO) 61.0-1.08 (3H, m), 2.4-2.5 (2H, m), 2.6-2.9 (2H, m), 4.3-4.8 (2H, m), 5.2-5.4 (2H, m), 6.15-6.25 (1H, m), 6.7-6.8 (1H, m), 7.3-7.4 (2H, m), 7.4-7.5 (3H, m), 8.2-8.25 (1H, m), 9.1-9.3 (1H, m); M+H 432.4, M−H 430.4.

Example II.20

3(R,S)-[3-Benzyloxy-2(S)-(2-oxo-3-propionylamino-2H-pyridin-1-yl)-propionylamino]-5-fluoro-4-oxo-pentanoic acid

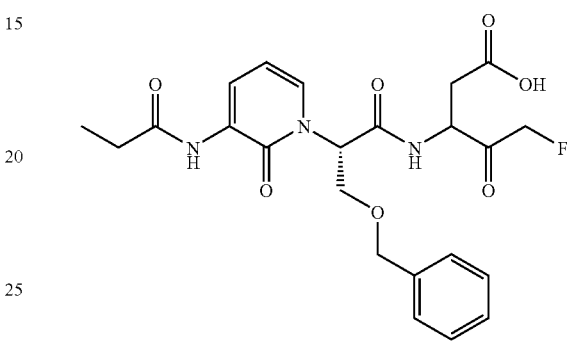

Prepared according to the methods A and D-G using (R)-3-Benzyloxy-2-hydroxy-propionic acid tert-butyl ester (prepared using a method similar to that reported in Lei et al., J. Carbohydrate Chemistry, 15, 4, 1996, 485-500) in method A; Off-white solid; $^1$H NMR (400 MHz, d6-DMSO) δ 1.05 (3H, t), 2.30-2.90 (4H, m), 3.95-4.15 (2H, m), 4.20-4.80 (4H, m), 5.05-5.40 (2H, m), 5.70 (1H, m), 6.35 (1H, m), 7.30 (5H, m), 7.40-7.55 (1H, m), 8.25 (1H, m), 8.95 (1H, m), 9.15 (1H, m); $^{19}$F (376 MHz, CDCl$_3$, proton-decoupled) δ−226.9, −232.9; M+H 476.3.

Example II.21

Enzyme Assays

The assays for caspase inhibition are based on the cleavage of a fluorogenic substrate by recombinant, purified human Caspases-1, -3, or -8. The assays are run in essentially the same way as those reported by Garcia-Calvo et al. (J. Biol. Chem. 273 (1998), 32608-32613), using a substrate specific for each enzyme. The substrate for Caspase-1 is Acetyl-Tyr-Val-Ala-Asp-amino-4-methylcoumarin. The substrate for Caspases-3 and -8 is Acetyl-Asp-Glu-Val-Asp-amino-4-methylcoumarin. Both substrates are known in the art.

The observed rate of enzyme inactivation at a particular inhibitor concentration, $k_{obs}$, is computed by direct fits of the data to the equation derived by Thornberry et al. (Biochemistry 33 (1994), 3943-3939) using a nonlinear least-squares analysis computer program (PRISM 2.0; GraphPad software). To obtain the second order rate constant, $k_{inact}$, $k_{obs}$ values are plotted against their respective inhibitor concentrations and $k_{inact}$ values are subsequently calculated by computerized linear regression.

Inhibition of caspases-1, -3, and -8 activity for selected compounds of this invention was determined by the above method. Compounds II.1-II.20 inhibited caspase-1 with a $k_{inact}$ of >60,000 M$^{-1}$s$^{-1}$, caspase-3 with a $k_{inact}$ between 0 and 300,000 M$^{-1}$s$^{-1}$, and caspase-8 with a $k_{inact}$ of at >35,000 M$^{-1}$s$^{-1}$.

Example II.22

PBMC Cell Assay

IL-1β Assay with a Mixed Population of Human Peripheral Blood Mononuclear Cells (PBMC) or Enriched Adherent Mononuclear Cells Processing of pre-IL-1β by ICE may be measured in cell culture using a variety of cell sources. Human PBMC obtained from healthy donors provides a mixed population of lymphocyte subtypes and mononuclear cells that produce a spectrum of interleukins and cytokines in response to many classes of physiological stimulators. Adherent mononuclear cells from PBMC provides an enriched source of normal monocytes for selective studies of cytokine production by activated cells.

Experimental Procedure:

An initial dilution series of test compound in DMSO or ethanol is prepared, with a subsequent dilution into RPMI-10% FBS media (containing 2 mM L-glutamine, 10 mM HEPES, 50 U and 50 ug/ml pen/strep) respectively to yield drugs at 4× the final test concentration containing 0.4% DMSO or 0.4% ethanol. The final concentration of DMSO is 0.1% for all drug dilutions. A concentration titration which brackets the apparent $K_i$ for a test compound determined in an ICE inhibition assay is generally used for the primary compound screen.

Generally 5-6 compound dilutions are tested and the cellular component of the assay is performed in duplicate, with duplicate ELISA determinations on each cell culture supernatant.

PBMC Isolation and IL-1 Assay:

Buffy coat cells isolated from one pint human blood (yielding 40-45 ml final volume plasma plus cells) are diluted with media to 80 ml and LeukoPREP separation tubes (Becton Dickinson) are each overlaid with 10 ml of cell suspension. After 15 min centrifugation at 1500-1800×g, the plasma/media layer is aspirated and then the mononuclear cell layer is collected with a Pasteur pipette and transferred to a 15 ml conical centrifuge tube (Corning). Media is added to bring the volume to 15 ml, gently mix the cells by inversion and centrifuge at 300×g for 15 min. The PBMC pellet is resuspended in a small volume of media, the cells are counted and adjusted to $6 \times 10^6$ cells/ml.

For the cellular assay, 1.0 ml of the cell suspension is added to each well of a 24-well flat bottom tissue culture plate (Corning), 0.5 ml test compound dilution and 0.5 ml LPS solution (Sigma #L-3012; 20 ng/ml solution prepared in complete RPMI media; final LPS concentration 5 ng/ml). The 0.5 ml additions of test compound and LPS are usually sufficient to mix the contents of the wells. Three control mixtures are run per experiment, with either LPS alone, solvent vehicle control, and/or additional media to adjust the final culture volume to 2.0 ml. The cell cultures are incubated for 16-18 hr at 37° C. in the presence of 5% $CO_2$.

At the end of the incubation period, cells are harvested and transferred to 15 ml conical centrifuge tubes. After centrifugation for 10 min at 200×g, supernatants are harvested and transferred to 1.5 ml Eppendorf tubes. It may be noted that the cell pellet may be utilized for a biochemical evaluation of pre-IL-1β and/or mature IL-1 content in cytosol extracts by Western blotting or ELISA with pre-IL-1β specific antisera.

Isolation of Adherent Mononuclear Cells:

PBMC are isolated and prepared as described above. Media (1.0 ml) is first added to wells followed by 0.5 ml of the PBMC suspension. After a one hour incubation, plates are gently shaken and nonadherent cells aspirated from each well. Wells are then gently washed three times with 1.0 ml of media and final resuspended in 1.0 ml media. The enrichment for adherent cells generally yields $2.5-3.0 \times 10^5$ cells per well. The addition of test compounds, LPS, cell incubation conditions and processing of supernatants proceeds as described above.

ELISA:

Quantikine kits (R&D Systems) may be used for the measurement of mature IL-1β. Assays are performed according to the manufacturer's directions. Mature IL-1β levels of about 1-3 ng/ml in both PBMC and adherent mononuclear cell positive controls are observed. ELISA assays are performed on 1:5, 1:10 and 1:20 dilutions of supernatants from LPS-positive controls to select the optimal dilution for supernatants in the test panel.

The inhibitory potency of the compounds can be represented by an $IC_{50}$ value, which is the concentration of inhibitor at which 50% of mature IL-1β is detected in the supernatant as compared to the positive controls.

The skilled practitioner realizes that values obtained in cell assays may depend on multiple factors. The values may not necessarily represent fine quantitative results.

Selected compounds of this invention have been tested for inhibition of IL-1 release from PBMCs with IC50 values between 300 nM and 10 μM.

Anti-Fas Induced Apoptosis Assay

Cellular apoptosis may be induced by the binding of Fas ligand (FasL) to its receptor, CD95 (Fas). CD95 is one of a family of related receptors, known as death receptors, which can trigger apoptosis in cells via activation of the caspase enzyme cascade. The process is initiated by the binding of the adapter molecule FADD/MORT-1 to the cytoplasmic domain of the CD-95 receptor-ligand complex. Caspase-8 then binds FADD and becomes activated, initiating a cascade of events that involve the activation of downstream caspases and subsequent cellular apoptosis. Apoptosis can also be induced in cells expressing CD95 e.g., the Jurkat E6.1 T cell lymphoma cell line, using an antibody, rather than FasL, to crosslink the cell surface CD95. Anti-Fas-induced apoptosis is also triggered via the activation of caspase-8. This provides the basis of a cell based assay to screen compounds for inhibition of the caspase-8-mediated apoptotic pathway.

Experimental Procedure

Jurkat E6.1 cells are cultured in complete medium consisting of RPMI-1640 (Sigma No)+10% foetal calf serum (Gibco BRL No. 10099-141)+2 mM L-glutamine (Sigma No. G-7513). The cells are harvested in log phase of growth. 100 ml of cells at $5-8 \times 10^5$ cells/ml are transferred to sterile 50 ml Falcon centrifuge tubes and centrifuged for 5 minutes at 100×g at room temperature. The supernatant is removed and the combined cell pellets resuspended in 25 ml of complete medium. The cells are counted and the density adjusted to $2 \times 10^6$ cells/ml with complete medium.

The test compound is dissolved in dimethyl sulfoxide (DMSO)(Sigma No. D-2650) to give a 100 mM stock solution. This is diluted to 400 μM in complete medium, then serially diluted in a 96-well plate prior to addition to the cell assay plate.

100 μl of the cell suspension ($2 \times 10^6$ cells) is added to each well of a sterile 96-well round-bottomed cluster plate (Costar No. 3790). 50 μl of compound solution at the appropriate dilution and 50 μl of anti-Fas antibody, clone CH-11 (Upstate, Cat No. 1 544 675) at a final concentration of 10 ng/ml, are added to the wells. Control wells are set up minus antibody and minus compound but with a serial dilution of DMSO as vehicle control. The plates are incubated for 16-18 hrs at 37° C. in 5% CO2 and 95% humidity.

Apoptosis of the cells is measured by the quantitation of DNA fragmentation using a 'Cell Death Detection Assay' from Roche diagnostics, No. 1544 675. After incubation for 16-18 hrs the assay plates are centrifuged at 100×g at room temperature for 5 minutes. 150 μl of the supernatant are removed and replaced by 150 μl of fresh complete medium. The cells are then harvested and 200 μl of the lysis buffer supplied in the assay kit are added to each well. The cells are triturated to ensure complete lysis and incubated for 30 minutes at 4° C. The plates are then centrifuged at 1900×g for 10 minutes and the supernatants diluted 1:20 in the incubation buffer provided. 100 μl of this solution is then assayed according to the manufacturer's instructions supplied with the kit. OD405 nm is measured 20 minutes after addition of the final substrate in a SPECTRAmax Plus plate reader (Molecular Devices). OD405 nm is plotted versus compound concentration and the IC50 values for the compounds are calculated using the curve-fitting program SOFTmax Pro (Molecular Devices) using the four parameter fit option. Selected compounds have been tested in this assay and shown to inhibit Fas-induced apoptosis of Jurkat cells with IC50 values between 0.013 μM and 8 μM.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

We claim:
1. A compound of formula I:

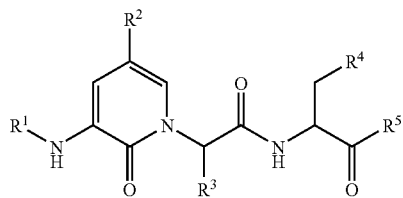

wherein:
$R^1$ is $R^6C(O)-$, $HC(O)-$, $R^6SO_2-$, $R^6OC(O)-$, $(R^6)_2NC(O)-$, $(R^6)(H)NC(O)-$, $R^6C(O)C(O)-$, $(R^6)_2NC(O)C(O)-$, $(R^6)(H)NC(O)C(O)-$, or $R^6OC(O)C(O)-$;
$R^2$ is hydrogen, $-CF_3$, -halo, $-OR^2$, $-NO_2$, $-OCF_3$, $-CN$, or $R^8$;
$R^3$ is optionally substituted (C6-C10)-aryl or -T-$R^9$;
$R^4$ is $-COOH$ or $-COOR^8$;
$R^5$ is $-CH_2F$ or $-CH_2O$-2,3,5,6-tetrafluorophenyl;
$R^6$ is $R^{6a}$ or $R^{6b}$;
$R^{6a}$ and $R^{6b}$ are each independently
(C1-C3)-aliphatic-,
(C4-C12)-aliphatic-,
(C3-C10)-cycloaliphatic-,
(C6-C10)-aryl-,
(C3-C10)-cycloaliphatic-(C1-C12)-aliphatic-, (C6-C10)-aryl-(C1-C12)-aliphatic-,
R is halogen, $-OR^7$, $-OC(O)N(R^7)_2$, $-NO_2$, $-CN$, $-CF_3$, $-OCF_3$, $-R^7$, oxo, thioxo, $=NR^7$, $=N(OR^7)$, 1,2-methylenedioxy, 1,2-ethylenedioxy, $-N(R^7)_2$, $-SR^7$, $-SOR^7$, $-SO_2R^7$, $-SO_2N(R^7)_2$, $-SO_3R^7$, $-C(O)R^7$, $-C(O)C(O)R^7$, $-C(O)C(O)OR^7$, $-C(O)C(O)N(R^7)_2$, $-C(O)CH_2C(O)R^7$, $-C(S)R^7$, $-C(S)OR^7$, $-C(O)OR^7$, $-OC(O)R^7$, $-C(O)N(R^7)_2$, $-OC(O)N(R^7)_2$, $-C(S)N(R^7)_2$, $-(CH_2)_{0-2}NHC(O)R^7$, $-N(R^7)N(R^7)COR^7$, $-N(R^7)N(R^7)C(O)OR^7$, $-N(R^7)N(R^7)CON(R^7)_2$, $-N(R^7)SO_2R^7$, $-N(R^7)SO_2N(R)_2$, $-N(R^7)C(O)OR^7$, $-N(R^7)C(O)R^7$, $-N(R^7)C(S)R^7$, $-N(R^7)C(O)N(R^7)_2$, $-N(R^7)C(S)N(R^7)_2$, $-N(COR^7)COR^7$, $-N(OR^7)R^7$, $-C(=NR^7)N(R^7)_2$, $-C(O)N(OR^7)R^7$, $-C(=NOR^7)R^7$, $-OP(O)(OR^7)_2$, $-P(O)(R^7)_2$, $-P(O)(OR^7)_2$, or $-P(O)(H)(OR^7)$;

each $R^7$ is independently selected from:
hydrogen-,
(C1-C12)-aliphatic-,
(C3-C10)-cycloaliphatic-,
(C3-C10)-cycloaliphatic-(C1-C12)-aliphatic-,
(C6-C10)-aryl-,
(C6-C10)-aryl-(C1-C12)aliphatic-,
wherein said cycloaliphatic is monocyclic or bicyclic, linearly fused, bridged, or spirocyclic, and wherein said aliphatic group is a straight-chained or branched alkyl, alkenyl, and alkynyl groups, wherein the alkenyl or alkynyl groups have a minimum of 2 carbon atoms;
wherein $R^7$ has up to 3 substituents selected independently from $J_2$; and
$J_2$ is halogen, $-OR^7$, $-OC(O)N(R^7)_2$, $-NO_2$, $-CN$, $-CF_3$, $-OCF_3$, $-R^7$, oxo, thioxo, $=N(R^7)$, $=NO(R^7)$, 1,2-methylenedioxy, 1,2-ethylenedioxy, $-N(R^7)_2$, $-SR^7$, $-SOR^7$, $-SO_2R^7$, $-SO_2N(R^7)_2$, $-SO_3R^7$, $-C(O)R^7$, $-C(O)C(O)R^7$, $-C(O)C(O)OR^7$, $-C(O)C(O)N(R)_2$, $-C(O)CH_2C(O)R^7$, $-C(S)R^7$, $-C(S)OR^7$, $-C(O)OR^7$, $-OC(O)R^7$, $-C(O)N(R^7)_2$, $-OC(O)N(R^7)_2$, $-C(S)N(R^7)_2$, $-(CH_2)_{0-2}NHC(O)R^7$, $-N(R^7)N(R^7)COR^7$, $-N(R^7)N(R^7)C(O)OR^7$, $-N(R^7)N(R^7)CON(R^7)_2$, $-N(R^7)SO_2R^7$, $-N(R^7)SO_2N(R)_2$, $-N(R^7)C(O)OR^7$, $-N(R^7)C(O)R^7$, $-N(R^7)C(S)R^7$, $-N(R^7)C(O)N(R^7)_2$, $-N(R^7)C(S)N(R^7)_2$, $-N(COR^7)COR^7$, $-N(OR^7)R^7$, $-CN$, $-C(=NR^7)N(R^7)_2$, $-C(O)N(OR^7)R^7$, $-C(=NOR^7)R^7$, $-OP(O)(OR^7)_2$, $-P(O)(R^7)_2$, $-P(O)(OR^7)_2$, or $-P(O)(H)(OR^7)$; and $R^8$ is (C1-C12)-aliphatic-,
(C3-C10)-cycloaliphatic-,
(C6-C10)-aryl-,
(C3-C10)-cycloaliphatic-(C1-C12)-aliphatic-,
(C6-C10)-aryl-(C1-C12)-aliphatic-,
wherein up to 3 aliphatic carbon atoms may be replaced with a group selected from O, N, N($R^7$), S, SO, and SO$_2$; and wherein $R^8$ is optionally substituted with up to 6 substituents independently selected from R;

T is (C1-C6) aliphatic wherein up to 2 aliphatic carbon atoms in T may be optionally replaced with S, SO, SO$_2$, O, N($R^7$), or N in a chemically stable arrangement; wherein each T may be optionally substituted with up to 3 R substituents;

$R^9$ is optionally substituted (C6-C10)-aryl,
wherein, unless otherwise indicated, optional substituents on an aliphatic, aryl, cycloaliphatic, are independently selected from R.

2. The compound according to claim 1 wherein $R^5$ is $-CH_2O$-2,3,5,6-tetrafluorophenyl.

3. The compound according to claim 1 wherein $R^5$ is $-CH_2F$.

4. The compound according to claim 1, wherein $R^1$ is $R^6C(O)-$, $(R^6)_2NC(O)-$, $R^6C(O)C(O)-$, $(R^6)_2NC(O)C(O)-$, $(R^6)(H)NC(O)C(O)-$, or $R^6OC(O)C(O)-$ wherein $R^6$ is $R^{6b}$.

5. The compound according to claim 1, wherein $R^1$ is $HC(O)-$, $R^6SO_2-$, $R^6OC(O)-$, or $(R^6)(H)NC(O)-$ wherein $R^6$ is $R^{6a}$.

6. The compound according to claim 4, wherein $R^1$ is $R^6C(O)-$.

7. The compound according to claim 5, wherein $R^1$ is $R^6SO_2-$.

8. The compound according to claim 4, wherein $R^1$ is $(R^6)_2NC(O)-$.

9. The compound according to claim 8, wherein $R^1$ is $(R^6)(H)NC(O)-$.

10. The compound according to claim 4, wherein $R^1$ is $(R^6)OC(O)-$.

11. The compound according to claim 4 or claim 5, wherein $R^{6a}$ is (C4-C12)-aliphatic-, (C3-C10)-cycloaliphatic-, (C6-C10)-aryl-, (C3-C10)-cycloaliphatic-(C1-C12)-aliphatic-, (C6-C10)-aryl-(C1-C12)-aliphatic-, wherein up to 3 aliphatic carbon atoms may be replaced by a group selected from O, N, N($R^7$), S, SO, and $SO_2$; and wherein $R^{6a}$ is independently substituted with up to 6 substituents independently selected from R;
$R^{6b}$ is $R^{6a}$ or (C1-C3)-aliphatic-.

12. The compound according to claim 11, wherein $R^{6a}$ is (C4)-aliphatic, (C3-C10)-cycloaliphatic-, (C6-C10)-aryl-, or (C6-C10)-aryl-(C1-C12)-alkyl-; wherein up to 3 aliphatic carbon atoms may be replaced by a group selected from O, N, N($R^7$), S, SO, and $SO_2$; and wherein $R^{6a}$ is optionally substituted.

13. The compound according to claim 12, wherein $R^{6a}$ is (C6-C10)-aryl-; wherein the aryl is optionally substituted.

14. The compound according to claim 12 or claim 13, wherein each $R^{6b}$ is $R^{6a}$ or (C1-C3)-aliphatic.

15. The compound according to claim 11, wherein $R^2$ is hydrogen, $CF_3$, or $CH_3$.

16. The compound according to claim 15, wherein $R^2$ is hydrogen or $CF_3$.

17. The compound according to claim 15, wherein T is (C1-C4) aliphatic wherein up to one aliphatic carbon atom may be replaced with a group selected from O, N, N($R^2$), and S.

18. The compound according to claims 17 wherein T is $-CH_2-$, $-CH(Me)-$, $-CH_2-CH_2-$, $-CH_2-O-CH_2-$, $-CH(Me)-O-CH_2-$, or $-CH_2-CH_2-O-CH_2-$.

19. The compound according to claim 17 wherein $R^3$ is T-$R^9$ and T is (C1-C4) aliphatic.

20. The compound according to claim 19, wherein T is $-CH_2-$ or $-CH_2-CH_2-$.

21. The compound according to claim 20, wherein T is $-CH_2-$.

22. The compound according to claim 17, wherein $R^9$ is an optionally substituted C6-aryl.

23. The compound according to claim 22, wherein $R^9$ is optionally substituted phenyl.

24. The compound according to claim 23, wherein $R^9$ is an unsubstituted phenyl.

25. The compound of claim 1, as represented by Formula II,

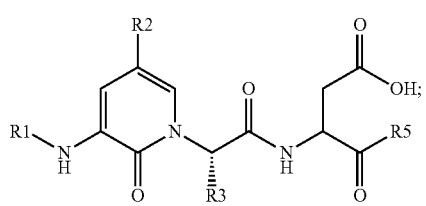

wherein $R^1$, $R^2$, $R^3$, and $R^5$ are as defined below:

| $R^1$ | $R^2$ | $R^3$ | $R^5$ |
|---|---|---|---|
| Ph(C=O)— | H | Bn | $CH_2F$ |
| Ph(C=O)— | H | $CH_2CH_2Ph$ | $CH_2F$ |
| Ph(C=O)— | $CH_3$ | Bn | $CH_2F$ |
| 2,6 dimethylphenyl(C=O)— | H | Bn | $CH_2F$ |
| 2,6 dichlorophenyl(C=O)— | H | Bn | $CH_2F$ |
| $(Et)_2N(C=O)-$ | H | Bn | $CH_2F$ |
| Bn(C=O)— | H | Bn | $CH_2F$ |
| 2,6 dichlorophenyl(C=O)— | H | Bn | $CH_2O$-2,3,4,5-tetrafluorophenyl |
| PhNH(C=O)— | H | Bn | $CH_2F$ |
| Ph(C=O) | $CF_3$ | Bn | $CH_2F$ |
| i-Pr(C=O)— | H | Bn | $CH_2F$ |
| Et(C=O)— | H | Bn | $CH_2F$ |
| Et($SO_2$)— | H | Bn | $CH_2F$ |
| Et(C=O)— | H | $(CH_2)_2$—OBn | $CH_2F$ |
| Et(C=O)— | H | CH(Me)—OBn | $CH_2F$ |
| Et(C=O)— | H | Ph | $CH_2F$ |
| Et(C=O)— | H | $CH_2OBn$ | $CH_2F$. |

26. A pharmaceutical composition comprising:
a) a compound according to claim 1; and
b) a pharmaceutically acceptable carrier, adjuvant or vehicle.

\* \* \* \* \*